US010085696B2

(12) United States Patent
Thakur et al.

(10) Patent No.: US 10,085,696 B2
(45) Date of Patent: Oct. 2, 2018

(54) DETECTION OF WORSENING HEART FAILURE EVENTS USING HEART SOUNDS

(71) Applicant: Cardiac Pacemakers, Inc., St. Paul, MN (US)

(72) Inventors: Pramodsingh Hirasingh Thakur, Woodbury, MN (US); Qi An, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/286,027

(22) Filed: Oct. 5, 2016

(65) Prior Publication Data

US 2017/0100081 A1      Apr. 13, 2017

Related U.S. Application Data

(60) Provisional application No. 62/238,953, filed on Oct. 8, 2015.

(51) Int. Cl.
*A61B 5/04* (2006.01)
*A61B 5/00* (2006.01)
(Continued)

(52) U.S. Cl.
CPC ........ *A61B 5/7282* (2013.01); *A61B 5/02028* (2013.01); *A61B 5/7275* (2013.01); *A61B 7/04* (2013.01); *A61N 1/36514* (2013.01); *A61N 1/37235* (2013.01); *A61N 1/3962* (2013.01); *A61N 1/3987* (2013.01); *H04L 67/12* (2013.01)

(58) Field of Classification Search
USPC .................................................. 600/513, 528
See application file for complete search history.

(56) References Cited

U.S. PATENT DOCUMENTS 7,731,658 B2   6/2010   Dalal et al.
7,736,319 B2   6/2010   Patangay et al.
(Continued)

FOREIGN PATENT DOCUMENTS

WO    WO-2017062446 A1    4/2017

OTHER PUBLICATIONS

Thakur, Pramodsingh Hirasingh, et al., "Predictions of Worsening Heart Failure", U.S. Appl. No. 15/281,992, filed Sep. 30, 2016.
(Continued)

*Primary Examiner* — Nicole F Johnson
(74) *Attorney, Agent, or Firm* — Schwegman Lundberg & Woessner, P.A.

(57) ABSTRACT

Systems and methods for detecting events indicative of worsening using heart sounds are disclosed. A system can include a signal sensor circuit to sense a heart sound (HS) signal. The system can detect at least first and different second HS components using the HS signal, and generate respective first and second HS metrics. The system can determine a trend indicator for the first or second HS metric, and selectively generate one or more composite HS metrics using the first and second HS metrics, according to the trend indicator indicating a growing or decay trend. The system can include a heart failure (HF) event detector to produce a HF status using the composite HS metrics, and output an indication of the HF status, or deliver therapy according to the HF status.

20 Claims, 10 Drawing Sheets

(51) Int. Cl.

| | | |
|---|---|---|
| *H04L 29/08* | (2006.01) | |
| *A61B 5/02* | (2006.01) | |
| *A61B 7/04* | (2006.01) | |
| *A61N 1/365* | (2006.01) | |
| *A61N 1/39* | (2006.01) | |
| *A61N 1/372* | (2006.01) | |

(56) References Cited

U.S. PATENT DOCUMENTS

| | | |
|---|---|---|
| 7,853,327 B2 | 12/2010 | Patangay et al. |
| 7,922,669 B2 | 4/2011 | Zhang et al. |
| 8,034,000 B2 | 10/2011 | Zhang et al. |
| 8,133,187 B2 | 3/2012 | Holmstrom et al. |
| 8,597,197 B2 | 12/2013 | Patangay et al. |
| 8,738,119 B2 | 5/2014 | Zhang et al. |
| 8,758,260 B2 | 6/2014 | Zhang et al. |
| 8,764,674 B2 | 7/2014 | Song et al. |
| 2004/0106961 A1 | 6/2004 | Siejko et al. |
| 2007/0027400 A1* | 2/2007 | Carlson ............ A61B 7/04 600/528 |
| 2008/0262368 A1 | 10/2008 | Patangay et al. |
| 2014/0277238 A1 | 9/2014 | An et al. |

OTHER PUBLICATIONS

"International Application Serial No. PCT/US2016/055486, International Search Report dated Jan. 5, 2017", 4 pgs.

"International Application Serial No. PCT/US2016/055486, Written Opinion dated Jan. 5, 2017", 5 pgs.

\* cited by examiner

DETECTION OF WORSENING HEART FAILURE EVENTS USING HEART SOUNDS

TECHNICAL FIELD

This application claims the benefit of priority under 35 U.S.C. § 119(e) of U.S. Provisional Patent Application Ser. No. 62/238,953, filed on Oct. 8, 2015, which is herein incorporated by reference in its entirety.

TECHNICAL FIELD

This document relates generally to medical devices, and more particularly, to systems, devices and methods for detecting and monitoring heart failure decompensation.

BACKGROUND

Congestive heart failure (CHF) is a major health problem and affects many people in the United States alone. CHF is the loss of pumping power of the heart, and may result in the inability to deliver enough blood to meet the demands of peripheral tissues. CHF patients can have enlarged heart with weakened cardiac muscles, and as a result, reduced contractility and poor cardiac output of blood.

CHF is usually a chronic condition, but can occur suddenly. It can affect the left heart, right heart or both sides of the heart. If CHF affects the left ventricle, signals that control the left ventricular contraction are delayed, and the left and right ventricles do not contract simultaneously. Asynchronous contractions of the left and right ventricles further decrease the pumping efficiency of the heart.

Overview

Frequent monitoring of CHF patients and timely detection of events indicative of heart failure (HF) decompensation status can help prevent worsening of HF in CHF patients, hence reducing cost associated with HF hospitalization. Additionally, identification of patient at an elevated risk of developing future HF events such as worsening of HF can help ensure timely treatment, thereby improving the prognosis and patient outcome. Identifying and safely managing the patients having risk of future HF events can avoid unnecessary medical intervention and reduce healthcare cost.

Ambulatory medical devices can be used for monitoring HF patient and detecting HF decompensation events. Examples of such ambulatory medical devices can include implantable medical devices (IMD), subcutaneous medical devices, wearable medical devices or other external medical devices. The ambulatory or implantable medical devices can include physiologic sensors which can be configured to sense electrical activity and mechanical function of the heart, or physical or physiological variables associated with the signs and symptoms of worsening of HF. The medical device can optionally deliver therapy such as electrical stimulation pulses to a target area, such as to restore or improve the cardiac function or neural function. Some of these devices can provide diagnostic features, such as using transthoracic impedance or other sensor signals. For example, fluid accumulation in the lungs decreases the transthoracic impedance due to the lower resistivity of the fluid than air in the lungs. Fluid accumulation in the lungs can also irritate the pulmonary system and leads to decrease in tidal volume and increase in respiratory rate.

Some ambulatory medical devices can include a physiologic sensor for detecting heart sounds. One type of such physiologic sensor is a sensor for sensing heart sounds. Heart sounds are associated with mechanical vibrations from activity of a patient's heart and the flow of blood through the heart. Heart sounds recur with each cardiac cycle and are separated and classified according to the activity associated with the vibration. The first heart sound (S1) is associated with the vibrational sound made by the heart during tensing of the mitral valve. The second heart sound (S2) marks the beginning of diastole. The third heart sound (S3) and can be related to filling pressures of the left ventricle during diastole. The fourth heart sound (S4) is associated with atria contraction such as to overcome an abnormally stiff ventricle. Heart sounds are useful indications of proper or improper functioning of a patient's heart. The fluid accumulation in the lungs in HF patients can result in an elevation of ventricular filling pressure, resulting in a louder S3 heart sound.

Worsening of HF status can deteriorate diastolic function of the heart. Monitoring and trending the S3 heart sound can be useful in assessing the diastolic function of the heart and the progression of HF status. Accurate and timely detection of worsening of HF such as HF decompensation events, or reliable prediction of the risk of a patient developing future HF decompensation event may require reliable sensing of S3 heart sound and determination of the trend of S3 strength as a function of time. However, S3 is generally a weak signal compared to S1 or S2 heart sounds. S3 can be contaminated by noise or other interferences, or be affected by various physiologic or environmental conditions. As such, the reliability of the detected S3 strength or the trend of the S3 can be compromised, a S3 heart sound based HF decompensation detection algorithm may produce false positive or false negative detections, and a S3 heart sound based HF risk stratification algorithms can provide less desirable prediction performance. Therefore, there remains a considerable need of systems and methods that can reliably and accurately detect and trend the S3 heart sound for the use in detecting worsening of HF or identifying CHF patients with elevated risk of developing future events of worsening of HF.

The present inventors have also recognized that different heart sound components, such as S1 and S3 heart sounds, can manifest certain temporal pattern of covariation. The trend of a heart sound component, or the trend of covariation among two or more heart sound components, can be predictive of worsening HF events. The present inventors have recognized that some CHF patients may demonstrate concurrent growth trends of S1 amplitude and S3 amplitude over time. However, some other CHF patients may demonstrate a different covariation pattern such as opposite trends of HS components, such as a decay trend of S1 amplitude accompanied by a growth trend of S3 amplitude. Patients with different covariation pattern of HS components may require different management or treatment plans.

Various embodiments described herein can help improve detection of an event indicative of worsening of HF, or improve process of identifying patients at elevated risk of developing future HF events. The present document discusses, among other things, systems and methods for detecting events indicative of worsening HF. A system can include a signal sensor circuit to sense a heart sound (HS) signal. The system can detect at least first and different second HS components using the HS signal, and generate respective first and second HS metrics. The system can determine a trend indicator for the first or second HS metric, and selectively generate one or more composite HS metrics using the first and second HS metrics, according to the trend indicator indicating a growing or decay trend. The system can include a heart failure (HF) event detector to detect a HF status using the composite HS metrics, and output an indication of the HF status, or deliver therapy according to the HF status.

In Example 1, a system can comprise a signal sensor circuit that can sense a heart sound (HS) signal from a patient, a memory circuit, a HS component detector circuit, a HS metric generator circuit, a blending circuit, a heart failure (HF) event detector circuit, and an output circuit. The HS component detector circuit can be coupled to the signal sensor circuit and the memory circuit to detect at least first and different second HS component from the received HS signal. The HS metric generator circuit can be coupled to the HS component detector circuit to use the detected first and second HS components to respectively generate first and second HS metrics stored in the memory circuit. The blending circuit can be coupled to the memory circuit or the HS metric generator circuit to generate one or more composite HS metrics using the first and second HS metrics. The failure (HF) event detector circuit can include a comparator circuit coupled to the blending circuit to detect a HF status when the one or more composite HS metrics satisfy at least one criterion. The output circuit can output an indication of the HF status.

Example 2 can include, or can optionally be combined with the subject matter of Example 1 to optionally include a trending circuit coupled to the HS metric generator circuit. The trending circuit can determine a trend indicator that can be stored in the memory circuit. The trend indicator indicates a temporal pattern of at least one of the first or second HS metric. The blending circuit can selectively generate the one or more composite HS metrics according to the trend indicator.

Example 3 can include, or can optionally be combined with the subject matter of Example 2 to include, the blending circuit that can selectively generate the one or more composite HS metrics including a first composite HS metric when the trend indicator indicates a first trend, or a different second composite HS metric when the trend indicator indicates a different second trend.

Example 4 can include, or can optionally be combined with the subject matter of Example 3 to include, the HS component detector circuit that can detect the first HS component including a S1 or S2 heart sound and the second HS component including a S3 or S4 heart sound, and the HS metric generator circuit that can generate the first HS metric indicative of intensity of the detected S1 or S2 heart sound and the second HS metric indicative of intensity of the detected S3 or S4 heart sound.

Example 5 can include, or can optionally be combined with the subject matter of Example 4 to include, the HS metric generator circuit that can generate the first HS metric including an amplitude of S1 heart sound, and the second HS metric including an amplitude of S3 or S4 heart sound.

Example 6 can include, or can optionally be combined with the subject matter of one or any combination of Examples 4 or 5 to include: the trending circuit that can determine the trend indicator including a S1 intensity trend indicating a decay trend or a growth trend of the S1 intensity over a specified period of time; and the blending circuit that can selectively generate the first composite HS metric that is proportional to a ratio of the intensity of S3 or S4 heart sound to the intensity of S1 heart sound if the trend indicator indicates a decay trend of the intensity of S1 heart sound, or the second composite HS metric that is proportional to a product of the intensity of S3 or S4 heart sound and the intensity of S1 heart sound if the trend indicator indicates a growth trend of the intensity of S1 heart sound.

Example 7 can include, or can optionally be combined with the subject matter of one or any combination of Examples 4 or 5 to include: the trending circuit that can determine the trend indicator including a covariation temporal pattern between the intensity of S1 heart sound and the intensity of the S3 or S4 heart sound over a specified period of time; and the blending circuit that can selectively generate the first composite HS metric that is proportional to a ratio of the intensity of S3 or S4 heart sound to the intensity of S1 heart sound if the trend indicator indicates a growth trend of S3 or S4 intensity concurrent with a decay trend of S1 intensity, or the second composite HS metric that is proportional to a product of the intensity of S3 or S4 heart sound and the intensity of S1 heart sound if the trend indicator indicates a growth trend of S3 or S4 intensity concurrent with a growth trend of S1 intensity.

Example 8 can include, or can optionally be combined with the subject matter of one or any combination of Examples 1 through 7 to include, a classifier circuit configured to classify the detected HF status into one of a first category of HF with cardiac contractility compensation (CCC), or a second category of HF without CCC.

Example 9 can include, or can optionally be combined with the subject matter of Example 8 to include, the HS metric generator circuit that can generate the first HS metric including a S1 intensity, and the classifier circuit that can classify the detected HF status into the first category of HF with CCC if the S1 intensity satisfies a first criterion, or to classify the detected HF status into the second category of HF without CCC if the S1 intensity satisfies a second criterion.

Example 10 can include, or can optionally be combined with the subject matter of Example 9 to optionally include, the classifier circuit that can classify the detected HF status into the first category of HF with CCC if the S1 intensity has a growth trend over time, or classify the detected HF status into the second category of HF without CCC if the S1 intensity has a decay trend over time.

Example 11 can include, or can optionally be combined with the subject matter of Example 8 to optionally include: the HS metric generator circuit that can generate the composite HS metric proportional to a ratio of the intensity of S3 or S4 heart sound to the intensity of S1 heart sound, or proportional to a product of the intensity of S3 or S4 heart sound and the intensity of S1 heart sound; and the classifier circuit that can classify the detected HF status into the first category of HF with CCC if the composite HS metric satisfies a first criterion, or to classify the detected HF status into the second category of HF without CCC if the composite HS metric satisfies a second criterion.

Example 12 can include, or can optionally be combined with the subject matter of one or any combination of Examples 1 through 11 to include, at least one of the first or second HS metric that includes an intensity measure of a portion of the HS signal, where the portion of HS signal includes at least a portion of a specified HS component.

Example 13 can include, or can optionally be combined with the subject matter of one or any combination of Examples 1 through 12 to include, the signal sensor circuit that can receive a physiological signal sensed from the patient and different from the HS signal and indicative of cardiac contractility.

Example 14 can include, or can optionally be combined with the subject matter of one or any combination of Examples 1 through 13 to include, a therapy circuit configured to deliver a therapy to the patient in response to the HF status satisfying at least one condition.

Example 15 can include, or can optionally be combined with the subject matter of Example 14 to optionally include, the therapy circuit that can deliver a first therapy in response to a detection of HF with cardiac contractility compensation (CCC), or deliver a second therapy in response to a detection of HF without CCC, the second therapy being more aggressive than the first therapy.

In Example 16, a method can comprise steps of: sensing a heart sound (HS) signal from a patient using a HS sensor; detecting at least a first and a different second HS components from the sensed HS signal; generating first and second HS metrics respectively from the detected first and second HS components; generating one or more composite HS metrics using the first and second HS metrics; detecting a HF status when the one or more composite HS metrics satisfy at least one criterion; and outputting an indication of the HF status.

Example 17 can include, or can optionally be combined with the subject matter of Example 16 to optionally include, determining a trend indicator indicating a temporal pattern of at least one of the first or second HS metric. The generation of the one or more composite HS metrics can include generating a first composite HS metric when the trend indicator indicates a first trend, or generating a different second composite HS metric when the trend indicator indicates a different second trend.

Example 18 can include, or can optionally be combined with the subject matter of Example 17 to optionally include, detecting the first HS component including a S1 heart sound, and detecting the second HS component including a S3 or S4 heart sound. The first HS metric can include an intensity metric of the detected S1 heart sound, and the second HS metric can include an intensity metric of the detected S3 or S4 heart sound.

Example 19 can include, or can optionally be combined with the subject matter of Example 18 to optionally include, determining the trend indicator includes a S1 intensity trend indicating a temporal pattern of the intensity of S1 heart sound over a specified period of time. The generation of the one or more composite HS metrics can include generating the first composite HS metric that is proportional to a ratio of the intensity of S3 or S4 heart sound to the intensity of S1 heart sound, when the trend indicator indicates a decay trend of the intensity of S1 heart sound, or generating the second composite HS metric that is proportional to a product of the intensity of S3 or S4 heart sound and the intensity of S1 heart sound, when the trend indicator indicates a growth trend of the intensity of S1 heart sound.

Example 20 can include, or can optionally be combined with the subject matter of Example 18 to optionally include, determining the trend indicator includes a covariation temporal pattern between the intensity of S1 heart sound and the intensity of the S3 or S4 heart sound over a specified period of time. The generation of the one or more composite HS metrics can include generating the first composite HS metric that is proportional to a ratio of the intensity of S3 or S4 heart sound to the intensity of S1 heart sound, when the trend indicator indicates a growth trend of S3 or S4 intensity concurrent with a decay trend of S1 intensity, or generating the second composite HS metric that is proportional to a product of the intensity of S3 or S4 heart sound and the intensity of S1 heart sound, when the trend indicator indicates a growth trend of S3 or S4 intensity concurrent with a growth trend of S1 intensity.

Example 21 can include, or can optionally be combined with the subject matter of Example 16 to optionally include, steps of classifying the detected HF status into a first category of HF with cardiac contractility compensation (CCC) if a HS metric satisfies a first criterion, or classifying the detected HF status into a second category of HF without CCC if the HS metric satisfies a second criterion.

Example 22 can include, or can optionally be combined with the subject matter of Example 21 to optionally include, classifying the detected progression of HF status that can include classifying the detected HF status into the first category of HF with CCC if the S1 intensity has a growth trend over time, or classifying the detected HF status into the second category of HF without CCC if the S1 intensity has a decay trend over time.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for detecting events indicative of worsening using heart sounds are disclosed. The heart sounds discussed in this document can include audible or inaudible mechanical vibrations caused by cardiac activity. Such mechanical vibrations can be conceptualized as providing acoustic energy. According to the present document, at least first and different second HS components can be detected, and respective first and second HS metrics can be generated. The system can generate one or more composite HS metrics using the first and second HS metrics. The system can include a heart failure (HF) event detector to detect a HF status using the composite HS metrics.

Figure 1:
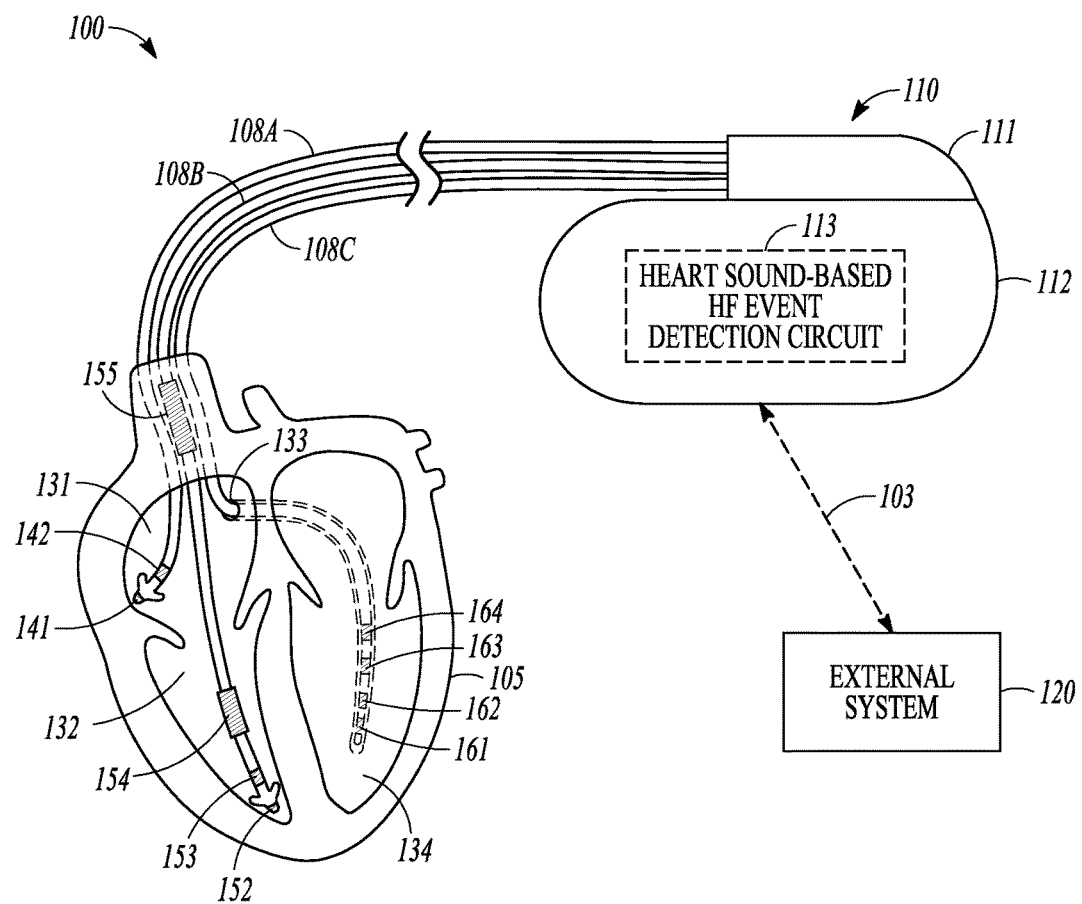
FIG. 1 illustrates generally an example of a Cardiac Rhythm Management (CRM) system and portions of an environment in which the CRM system can operate.

FIG. 1 illustrates generally an example of a Cardiac Rhythm Management (CRM) system 100 and portions of an environment in which the CRM system 100 can operate. The CRM system 100 can include an ambulatory medical device, such as an implantable medical device (IMD) 110 that can be electrically coupled to a heart 105 such as through one or more leads 108A-C, and an external system 120 that can communicate with the IMD 110 such as via a communication link 103. The IMD 110 may include an implantable cardiac device such as a pacemaker, an implantable cardioverter-defibrillator (ICD), a subcutaneously implantable cardioverter-defibrillator (S-ICD), or a cardiac resynchronization therapy defibrillator (CRT-D). It is also contemplated that, in other examples, the IMD 110 can include one or more monitoring or therapeutic devices such as a subcutaneously implanted device, a neural stimulator, a drug delivery device, a biological therapy device, a diagnostic device, or one or more other ambulatory medical devices. The IMD 110 may be coupled to, or may be substituted by a monitoring medical device such as a bedside or other external monitor. It is further contemplated that the device may not be an implantable device, but instead may be an external device. For example, the ambulatory medical device can include an external monitoring or therapeutic devices such as, for example, a wearable monitoring device or a wearable cardioverter defibrillator.

As illustrated in FIG. 1, the IMD 110 can include a hermetically sealed can 112 that can house an electronic circuit that can sense a physiological signal in the heart 105 and can deliver one or more therapeutic electrical pulses to a target region, such as in the heart, such as through one or more leads 108A-C. The CRM system 100 can include only one lead such as 108B, or can include two leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first pacing-sensing electrode 141 that can be located at or near its distal end, and a second pacing-sensing electrode 142 that can be located at or near the electrode 141. The electrodes 141 and 142 can be electrically connected to the IMD 110 such as via separate conductors in the lead 108A, such as to allow for sensing of the right atrial activity and optional delivery of atrial pacing pulses. The lead 108B can be a defibrillation lead that can include a proximal end that can be connected to IMD 110 and a distal end that can be placed at a target location such as in the right ventricle (RV) 132 of heart 105. The lead 108B can have a first pacing-sensing electrode 152 that can be located at distal end, a second pacing-sensing electrode 153 that can be located near the electrode 152, a first defibrillation coil electrode 154 that can be located near the electrode 153, and a second defibrillation coil electrode 155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram and can optionally allow delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the IMD 110 and a distal end that can be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the IMD 110 such as via separate conductors in the lead 108C such as to allow for sensing of the LV electrogram and optionally allow delivery of one or more resynchronization pacing pulses from the LV. Additional electrodes can be included in or along the lead 108C. In an example, as illustrated in FIG. 1, a third electrode 163 and a fourth electrode 164 can be included in the lead 108. In some examples (not shown in FIG. 1), at least one of the leads 108A-C, or an additional lead other than the leads 108A-C, can be implanted under the skin surface without being within at least one heart chamber, or at or close to heart tissue.

The IMD 110 can include an electronic circuit that can sense a physiological signal. The physiological signal can include an electrogram or a signal representing mechanical function of the heart 105. The hermetically sealed can 112 may function as an electrode such as for sensing or pulse delivery. For example, an electrode from one or more of the leads 108A-C may be used together with the can 112 such as for unipolar sensing of an electrogram or for delivering one or more pacing pulses. A defibrillation electrode from the lead 108B may be used together with the can 112 such as for delivering one or more cardioversion/defibrillation pulses. In an example, the IMD 110 can sense impedance such as between electrodes located on one or more of the leads 108A-C or the can 112. The IMD 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiological signal can be sensed from one or more physiological sensors that can be integrated within the IMD 110. The IMD 110 can also be configured to sense a physiological signal from one or more external physiologic sensors or one or more external electrodes that can be coupled to the IMD 110. Examples of the physiological signal can include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, physical activity or exertion level, physiologic response to activity, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are possible.

As illustrated, the CRM system 100 can include a heart sound (HS)-based HF event detection circuit 113. The HS-based HF event detection circuit 113 can include a signal sensor circuit to sense a HS signal. The HS-based HF event detection circuit 113 can first and different second HS components using the HS signal, and generate respective first and second HS metrics. The HS-based HF event detection circuit 113 can include a blending circuit to selectively generate one or more composite HS metrics using the first and second HS metrics. The HS-based HF event detection circuit 113 can detect a HF status using the one or more composite HS metrics. The HF status can indicate one or more early precursors of a HF decompensation episode, or an event indicative of HF progression over time, such as recovery or worsening of HF status. Examples of HS-based HF event detection circuit 113 are described below, such as with reference to FIGS. 2-4.

The external system 120 can allow for programming of the IMD 110 and can receive information about one or more signals acquired by IMD 110, such as can be received via a communication link 103. The external system 120 can include a local external IMD programmer. The external system 120 can include a remote patient management system that can monitor patient status or adjust one or more therapies such as from a remote location.

The communication link 103 can include one or more of an inductive telemetry link, a radio-frequency telemetry link, or a telecommunication link, such as an internet connection. The communication link 103 can provide for data transmission between the IMD 110 and the external system 120. The transmitted data can include, for example, real-time physiological data acquired by the IMD 110, physiological data acquired by and stored in the IMD 110, therapy history data or data indicating IMD operational status stored in the IMD 110, one or more programming instructions to the IMD 110 such as to configure the IMD 110 to perform one or more actions that can include physiological data acquisition such as using programmably specifiable sensing electrodes and configuration, device self-diagnostic test, or delivery of one or more therapies.

The HS-based HF event detection circuit 113 may be implemented at the external system 120, which can be configured to perform HF risk stratification or HF event detection, such as using data extracted from the IMD 110 or data stored in a memory within the external system 120. Portions of HS-based HF event detection circuit 113 may be distributed between the IMD 110 and the external system 120.

Portions of the IMD 110 or the external system 120 can be implemented using hardware, software, or any combination of hardware and software. Portions of the IMD 110 or the external system 120 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 110, the CRM system 100 could include a subcutaneous medical device (e.g., subcutaneous ICD, subcutaneous diagnostic device), wearable medical devices (e.g., patch based sensing device), or other external medical devices.

Figure 2:
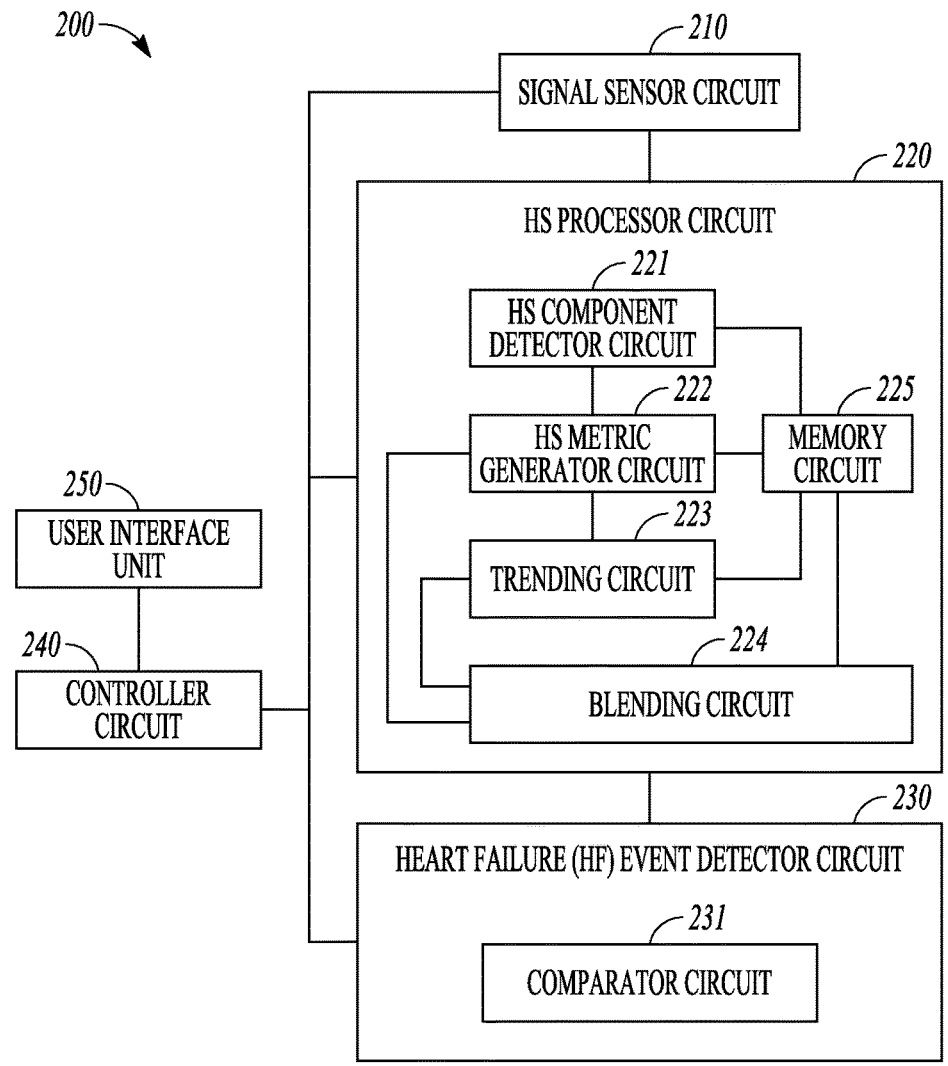
FIG. 2 illustrates generally an example of a heart sound (HS)-based physiologic event detector circuit.

FIG. 2 illustrates generally an example of a HS-based physiologic event detector circuit 200, which can be an embodiment of the HS-based HF event detection circuit 113. The HS-based physiologic event detector circuit 200 can also be implemented in an external system such as a patient monitor configured for providing the patient's diagnostic information to an end-user. The HS-based physiologic event detector circuit 200 can include one or more of a signal sensor circuit 210, a heart sound (HS) processor circuit 220, a heart failure (HF) event detector circuit 230, a controller circuit 240, and a user interface unit 250.

The signal sensor circuit 210 can sense HS information, such as information indicative of acoustic or mechanical activity of a heart. In an example, the HS information can include a HS waveform, such as a portion or entirety of a HS signal. The HS information can include information of at least one HS component, such as S1, S2, S3, or S4 heart sound. In an example, the HS waveform can include at least one ensemble average of a HS signal over multiple physiological cycles such as multiple cardiac cycles, or over a specified time period such as one minute, ten minutes, one hour, one day, etc.

The signal sensor circuit 210 can be coupled to one or more physiologic sensors that can be configured to sense, detect, or otherwise obtain HS information from a subject. Such physiologic sensors, hereinafter referred to as "HS sensors", can be configured to sense an electrical or optical HS signal that includes information indicative of acoustic or mechanical vibration of a heart. The HS sensor can be an implantable, wearable, or otherwise ambulatory sensor, and placed external to the patient or implanted inside the body. In an example, the HS sensor can be included in at least one part of an implantable system, such as an implantable medical device, or a lead coupled to the implantable medical device. In an example, the signal sensor circuit 210 can be configured to receive the HS information from a device capable of collecting or storing the HS information. Examples of such a device can include an external programmer, an electronic medical record system, a memory unit, or other data storage devices.

Various physiologic sensors can be used to sense the HS signal. In an example, the HS sensor can include an accelerometer that can be configured to sense an acceleration signal indicative of the heart sound of the subject. In another example, the HS sensor can include an acoustic sensor that can be configured to sense an acoustic energy indicative of the heart sound of the subject. Other sensors, such as microphone, piezo-based sensor, or other vibrational or acoustic sensors can also be used to sense the HS signal.

The signal sensor circuit 210 can include a sense amplifier circuit that can pre-process a HS signal such as received from the signal sensor circuit 210. The pre-processing can include amplification, digitization, filtering, or other signal conditioning operations. In an example, the signal sensor circuit 210 can include a bandpass filter adapted to filter the received HS signal to a frequency range of approximately between 5 and 90 Hz. In another example, the signal conditioning circuit can include a bandpass filter adapted to filter the received HS signal to a frequency range of approximately between 9 and 90 Hz. In an example, the signal sensor circuit 210 can include a double or higher-order differentiator configured to calculate a double or higher-order differentiation of the received HS signal.

The HS processor circuit 220, coupled to the signal sensor circuit 210, can be configured to process the HS signal such as received from the signal sensor circuit 210 and generate one or more composite HS metrics for use in detecting a target physiologic event such as an event indicative of progression of heart failure (HF) status. The HS processor circuit 220 can be implemented as a part of a microprocessor circuit in the CRM system 100. The microprocessor circuit can be a dedicated processor such as a digital signal processor, application specific integrated circuit (ASIC), microprocessor, or other type of processor for processing information including heart sounds. Alternatively, the microprocessor circuit can be a general purpose processor that can receive and execute a set of instructions of performing the functions, methods, or techniques described herein.

In an example such as illustrated in FIG. 2, the HS processor circuit 220 can include circuit sets comprising one or more other circuits or sub-circuits, that may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

As illustrated in FIG. 2, the HS processor circuit 220 can include one or more of a HS component detector circuit 221, a HS metric generator circuit 222, a blending circuit 224, and a memory circuit 225. The HS processor circuit 220 can additionally include an optional trending circuit 223. The HS component detector circuit 221 can be coupled to the signal sensor circuit and the memory circuit 225, and configured to detect at least two heart sound components such as from the S1, S2, S3, or S4 heart sounds, using the processed HS signal. The HS component detector circuit 221 can detect the one or more HS component using respective HS detection windows. The HS detection windows can be determined with reference to a physiologic event such as R wave, Q wave, or QRS complexes obtained from an electrocardiogram or an intracardiac electrogram signal synchronously sensed with the HS signal. In an example, the HS component detector circuit 221 can calculate HS signal energy within the corresponding HS detection window, and detects the HS component in response to the calculated HS signal energy exceeding a specified threshold. In another example, the HS component detector circuit 221 can detect the HS component adaptively by tracking the temporal locations of the previously detected HS component. Examples of detecting HS component are described below, such as with reference to FIG. 3.

The HS metric generator circuit 222 can be coupled to the HS component detector circuit to generate one or more HS signal metrics using the HS components. The HS metrics can include temporal, statistical, or morphological features of one or more HS components. In intensity measurements of HS components, such as S1 intensity ($\|S1\|$), S2 intensity ($\|S2\|$), S3 intensity ($\|S3\|$), or S4 intensity ($\|S4\|$). Examples of the intensity of a HS component can include amplitude of a detected HS component in a time-domain HS signal, a transformed HS signal such as integrated HS energy signal, or in a frequency-domain HS signal such as the peak value of the power spectral density, or peak value of a generic measurement within the respective HS detection window, such as peak envelop signal or root-mean-squared value of the portion of the HS signal within the HS detection window. The intensity of a HS component can also include a slope or rate of change of signal amplitude or peak energy. In an example, the HS metric can include an intensity measure of a portion of the HS signal that includes at least a portion of a specified HS component, such as a root-mean-squared value of the HS signal portion between an R wave and a subsequent S1 heart sound, or between an R wave and a subsequent S2 heart sound, within the same cardiac cycle.

The HS metric generator circuit 222 can alternatively or additionally calculate a signal metric indicative of electro-mechanical coupling of the heart, such as a cardiac timing interval (CTI) measured between a cardiac electrical event such as detected from the cardiac electrical signal and a mechanical event such as detected from the HS signal. The CTI can include a pre-ejection period (PEP), a systolic timing interval (STI), or a diastolic timing interval (DTI), among others. The PEP represents the total duration of the electrical and mechanical events prior to ejection, and can be measured as the time duration from the onset of the QRS to the S1 heart sound, that is, PEP≈Q-S1 interval. Alternatively, the PEP can be measured from the ventricular pacing (Vp) signal to the beginning of ventricular ejection such as represented by the onset of S1 heart sound, that is, PEP≈Vp-S1 interval. The STI represents the duration of total electro-mechanical systole, and contains two major components, namely the PEP and the LVET. The STI can be measured as an interval from the onset of the QRS complex on the ECG or the atrial activation event in an intracardiac EGM to the S2 heart sound, that is, STI≈Q-S2 interval. In the case when the ventricle is paced (Vp), the STI can be measured from the ventricular pacing (Vp) signal to the end of ventricular ejection such as represented by the onset of S2 heart sound, that is, STI≈Vp-S2 interval. The DTI represents the duration of total electro-mechanical diastole. The DTI spans from the closure of the aortic valve to the onset of the atrial depolarization in the next cardiac cycle. In an example, the DTI can be measured as the interval from the S2 heart sound to the onset of the QRS complex on the ECG or the atrial activation event in an intracardiac EGM of the next cardiac cycle, that is, DTI≈S2-Q interval. In some examples, the HS metric generator circuit 222 can generate composite measures using two or more of the STI, the DTI, the PEP, the cardiac cycle (CL), or the LVET. Examples of the composite measures can include PEP/LVET ratio, STI/DTI ratio, STI/cycle length (CL) ratio, or DTI/CL ratio, among others.

When provided, the optional trending circuit 223 can be coupled to the HS metric generator circuit to determine a trend indicator using a plurality of measurements of the HS metrics, such as over multiple cardiac cycles or during a specified period of time. In one example, the trend indicator can indicate a temporal pattern of a particular HS metric. Examples of the trend indicator can include a growth trend indicating an increase of the corresponding HS metric over time, or a decay trend indicating a decrease of the corresponding HS metric over time. The temporal pattern can be computed as a slope of change of the corresponding HS metric, where a positive slope indicates a growth trend and a negative slope indicates a decay trend. In another example, the trend indicator can indicate a covariation temporal pattern among two or more HS metrics. The covariation temporal pattern can be represented as a combination of the temporal patterns of the two or more HS metrics during the same period of time. The covariation temporal pattern can alternatively be represented as correlation between the two or more HS metrics, where a positive correlation indicates identical trend among the two or more HS metrics (e.g., both HS metrics manifests growth trends), and a negative correlation indicates opposite trends among the two or more HS metrics (e.g., one HS metric manifests a growth trend, and the other HS metric manifests a decay trend). Examples of determining trend indicators are described below, such as with reference to FIG. 3.

The HS metric generator circuit 222 can be coupled to the memory circuit 225, which can store the first and second HS metrics. The optional trending circuit 223, when provided, can also be coupled to the memory circuit 225 that stores the trend indicator. The blending circuit 224 can be coupled to the memory circuit 225, or be coupled to the HS metric generator circuit 222 and the optional trending circuit 223. The blending circuit 224 can generate one or more composite HS metric using two or more HS metrics such as produced by the HS metric generator circuit 222. A composite HS metric, denoted by Y, can be determined as a function of the two or more HS metrics $X_1, X_2, \ldots, X_N$, that is, $Y=f(X_1, X_2, \ldots, X_N)$, where the function $f$ can be a linear or nonlinear function. Examples of the linear functions can include weighted sum of the HS metrics, that is, $Y=\Sigma a_i X_i$ where $a_i$ denotes the weight factor for the HS metric $X_i$. Examples of the nonlinear functions can include at least one nonlinear term, such as a ratio $X_i/X_j$ or a product $X_i * X_j$ between two HS metrics $X_i$ and $X_j$, among others. In an example, the composite HS metric Y can be proportional to a ratio between two HS metrics, that is, $Y=k*X_i/X_j$, or proportional to a product between two HS metrics, that is, $Y=k*X_i*X_j$, where k is a scaling factor.

In an example, the blending circuit 224 can use the trend indicator such as produced by the optional trending circuit 223 to generate the one or more composite HS metric. The blending circuit 224 can generate different composite HS metrics in response to the temporal pattern of a HS metric, or the covariation temporal pattern among two or more HS metrics, as produced by the optional trending circuit 223. In an example, the blending circuit 224 can generate a first composite HS metric if the optional trending circuit 223 produces a HS trend indicator indicating a first trend, or generate a different second composite HS metric if the trend indicator indicates a different second trend. Examples of the composite HS metrics based on the HS trend indicator are described below, such as with reference to FIG. 3.

The heart failure (HF) event detector circuit 230 can be configured to detect a HF status using one or more HS metrics, one or more composite HS metrics such as produced by the blending circuit 224, or a combination of at least one HS metric and at least one composite HS metric. In an example, the HF event detector circuit 230 can generate a trend of at least one composite HS metric using multiple values of the composite HS metric obtained during multiple specified time periods. The HF event detector circuit 230 can include a comparator circuit 231 that can compare the one or more HS metrics or the one or more composite HS metrics to a criterion, such as a threshold value, to determine whether a HF decompensation event or other events indicative of worsening HF have occurred. In an example, the HF event detector circuit 230 can compute a weighted combination, such as exponentially weighted combination, of relative difference between one or more short-term values of a HS metric or a composite HS metric and one or more long-term baseline values of the HS metric or the composite HS metric, such as that disclosed in the commonly assigned U.S. Pat. Application Ser. No. 62/236, 416, entitled "PREDICTIONS OF WORSENING HEART FAILURE," which is hereby incorporated by reference in its entirety. In an example, the HF event detector circuit 230 can transform, such as by normalizing amplitudes of, one or both of the short-term values or the long-term baseline values of the HS metric or the composite HS metric before computing the relative difference between the short-term and long-term values.

In addition to or in lieu of detecting HF events, the HS-based physiologic event detector circuit 200 can include a detector configured to detect other types of physiologic events or conditions, such as indicative of an onset, termination, or progression (such as worsening or recovery) of a disease state including pulmonary edema, myocardial infarction, among others. In an example, the HS-based physiologic event detector circuit 200 can optionally include a therapy circuit coupled to the HF event detector circuit 230. The therapy circuit can be configured to deliver a therapy to the patient in response to the detected HF status. Examples of the therapy can include cardiac electrostimulation therapy, cardioversion therapy, defibrillation therapy, neuromodulation therapy, or other stimulation therapies using a specified energy source. The therapy circuit can be coupled to one or more electrodes disposed at one or more target sites in or on the patient's body, such as the electrodes on one or more of the leads 108A-C or the can housing 112. The therapy can be automatically delivered such as in response to the detection of a HF event such as a HF decompensation event, or it can be delivered upon receiving a user instruction that confirms the therapy. In some examples, the therapy circuit can be configured to receive user instructions, such as from the user interface unit 250, on programming one or more therapy parameters and delivering the programmed therapy to a target site in a patient. Examples of the therapy parameters can include pulse amplitude, pulse waveform, pulse frequency, pulse width, duty cycle, duration, or any other parameters associated with the electrostimulation. Programming of the therapy parameters can be based on information including one or more of the HS metrics, the HS trend indicator, or the composite HS metrics. The HS-based physiologic event detector circuit 200 can additionally generate human-perceptible alert or notification to inform system user such as a clinician to initiate or modify treatment of the patient.

The controller circuit 240 can control the operations of the signal sensor circuit 210, the HS processor circuit 220, the HF event detector circuit 230, and the data flow and instructions between these components. The controller circuit 240 can receive external programming input from the user interface unit 250 to control one or more of receiving HS signals, processing the HS signals to generate signal metrics, HS trend indicators, and the composite HS metrics, or detecting HF events. The user interface unit 250 can be configured to present programming options to the user and receive user's programming input. The user interface unit 250 can include an input device, such as a keyboard, on-screen keyboard, mouse, trackball, touchpad, touchscreen, or other pointing or navigating devices. The input device can enable a system user to program the parameters used for sensing the physiological signals. The user interface unit 250 can include an output unit that can produce a presentation of information including the detected HF status, such as in a textual, tabular or graphical format for displaying to a system user. The presentation of the output information can include audio or other human-perceptible media format to alert the system user of the detected HF status. In an example, at least a portion of the user interface unit 250, such as the user interface, can be implemented in the external system 120.

Figure 3:
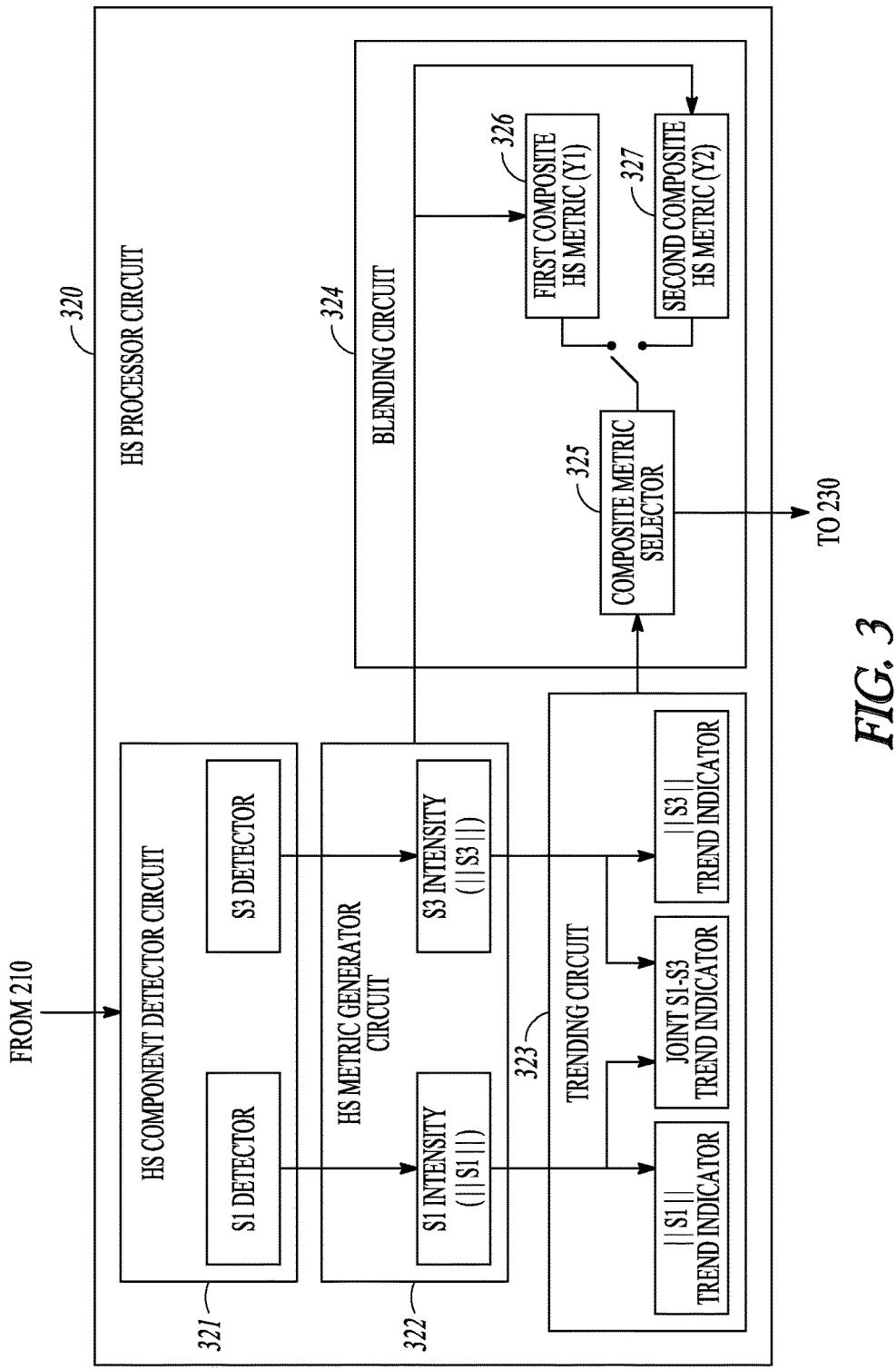
FIG. 3 illustrates generally an example of a HS processor circuit.

FIG. 3 illustrates generally an example of a HS processor circuit 320, which can be an embodiment of the HS processor circuit 220. The HS processor circuit 320 can include one or more of a HS component detector circuit 321, a HS metric generator circuit 322, and a blending circuit 324. The HS processor circuit 320 can include an optional trending circuit 323.

The HS component detector circuit 321, which can be an embodiment of the HS component detector circuit 221, can include a S1 detector configured to detect S1 heart sound, and a S3 detector configured to S3 heart sound, such as by using respective S1 detection window and S3 detection window. In an example, a S1 detection window can begin at 50 milliseconds (msec) following a detected R wave of a ECG signal and have a duration of 300 msec. An S2 detection window can begin at specified offset following a detected R wave or S1 heart sound. An S3 detection window can be determined using at least one cardiac signal feature such as the R-wave timing or the timing of S2 heart sound. The S3 detection window can have a specified duration and can begin at a specified offset following the detected S2. In an example, the offset can be 125 msec, and the S3 window duration can be 125 msec. The offset or the S3 window duration can be a function of a physiologic variable such as a heart rate. For example, the offset can be inversely proportional to the heart rate, such that the S3 detection window can start at a smaller offset following the S2 at a higher heart rate. The signal energy within the respective HS detection windows can be computed and compared to respective threshold value to detect S1 and S3 heart sounds. Alternatively, the HS component detector circuit 321 can detect S3 heart sound by adaptively tracking the timing of historically detected S3 heart sounds. A dynamic programming algorithm can be used to detect and track the S3 heart sound within the S3 detection window, such as that disclosed in the commonly assigned Patangay et al. U.S. Pat. No. 7,853,327 entitled "HEART SOUND TRACKING SYSTEM AND METHOD," which is hereby incorporated by reference in its entirety.

The HS metric generator circuit 322, which can be an embodiment of the HS metric generator circuit 222, can generate the HS metrics including S1 intensity ($\|S1\|$) indicative of peak amplitude or peak signal energy within the S1 detection window, and S3 intensity ($\|S3\|$) indicative of peak amplitude or peak signal energy within the S3 detection window. The HS metric generator circuit 322, which can be an embodiment of the HS metric generator circuit 222, can receive a plurality of S1 intensity measurements $\{\|S1\|_i\}$ for $i=1, 2, \ldots M$, such as over M cardiac cycles or during a specified period of time no shorter than M cardiac cycles. During the same specified time period or the same M cardiac cycles, the optional trending circuit 323, when provided, can receive a plurality of S3 intensity measurements $\{\|S3\|_i\}$ for $i=1, 2, \ldots, M$. The optional trending circuit 323 can use the received plurality of measurements $\{\|S1\|_i\}$ or $\{\|S3\|_i\}$ to generate an $\|S1\|$ trend indicator, a $\|S3\|$ trend indicator, or a joint S1-S3 trend indicator that indicates a covariation temporal pattern between the S1 intensity $\|S1\|$ and the S3 intensity $\|S3\|$. For example, in a patient who experiences worsening HF or an impending HF decompensation event, the optional trending circuit 323 may detect a growth trend of $\|S3\|$, denoted by "$\|S3\|^+$", as manifested by an increase of S3 intensity during a specified period of time. In another example, the optional trending circuit 323 may detect a decay trend of $\|S1\|$, denoted by "$\|S1\|^-$" as manifested by a decrease of S1 intensity over time. In some HF patients, a growth trend of $\|S3\|$ can be accompanied by concurrent decay trend of $\|S1\|$, the HS trend indicator can generate accordingly a joint S1-S3 trend indicator as denoted by ($\|S3\|^+$, $\|S1\|^-$), which indicates concurrent increase in $\|S3\|$ and decrease in $\|S1\|$ over the specified period of time.

The blending circuit 324, which can be an embodiment of the blending circuit 224, can selectively generate a first composite HS metric 326 (denoted by "Y1"), or a second composite HS metric 327 (denoted by "Y2"). The first composite HS metric 326 can be proportional to a ratio of $\|S3\|$ to $\|S1\|$, that is, $Y1=a*\|S3\|/\|S1\|$. The second composite HS metric 327 can be proportional to a product of $\|S3\|$ and $\|S1\|$, that is, $Y2=b*\|S3\|*\|S1\|$, where "a" and "b" are known scaling factors. The ratio $\|S3\|/\|S1\|$, or the product $\|S3\|*\|S1\|$, can be computed for each S1 component and S3 component detected within the same cardiac cycle. Alternatively, either or both of $\|S3\|$ and $\|S1\|$ can be determined using multiple measurements of the corresponding HS components such as over multiple cardiac cycles.

The blending circuit 324 can include a composite metric selector 325 coupled to the optional trending circuit 323. The composite metric selector 325 can select one of the first composite HS metric 326 or the second composite HS metric 327. The selection can be based on the trend indicator provided by the optional trending circuit 323. In an example, the composite metric selector 325 can select a composite HS metric, between Y1 and Y2, based on the $\|S1\|$ trend indicator. For example, if the $\|S1\|$ trend indicator indicates a decay trend of $\|S1\|$ or a negative slope of change of $\|S1\|$ over time, the first composite HS metric Y1 can be selected. If the $\|S1\|$ trend indicator indicates a growth trend of $\|S1\|$ or a positive slope of change of $\|S1\|$ over time, the second composite HS metric Y2 can be selected. That is, the composite metric selector 325 selects the composite HS metric (Y) as follows:

$$Y = \begin{cases} Y1 = a * \dfrac{\|S3\|}{\|S1\|}, & \text{if } \|S1\|^- \\ Y2 = b * \|S3\| * \|S1\|, & \text{if } \|S1\|^+ \end{cases}$$

In another example, the composite metric selector 325 can select the composite HS metric based on the joint S1-S3 trend indicator. For example, if the joint S1-S3 trend indicator indicates a decay trend of ||S1|| concurrent with a growth trend of ||S3||, then Y1 can be selected. If the joint S1-S3 trend indicator indicates a growth trend of ||S1|| concurrent with a growth trend of ||S3||, then Y2 can be selected. That is, the composite metric selector 325 selects the composite HS metric (Y) as follows:

$$Y = \begin{cases} Y1 = a * \frac{\|S3\|}{\|S1\|}, & \text{if } (\|S1\|^- \text{ and } \|S1\|^+) \\ Y2 = b * \|S3\| * \|S1\|, & \text{if } (\|S1\|^+ \text{ and } \|S1\|^+) \end{cases}$$

In an example, the composite metric selector 325 can select among the HS metrics (such as ||S1|| and ||S3||) and the first and second composite HS metrics. The selection can be based on the trend indicator provided by the optional trending circuit 323, such as the ||S1|| trend indicator or the joint S1-S3 trend indicator, as previously discussed. For example, the composite metric selector 325 can select the HS metric (Y) as follows:

$$Y = \begin{cases} Y1 = a * \frac{\|S3\|}{\|S1\|}, & \text{if } \|S1\|^- \\ Y2 = b * \|S3\|, & \text{if } \|S1\|^+ \end{cases}$$

The present inventors have recognized that when S1 intensity experiences a trend of decay (i.e., decrease in intensity with time), a composite HS metric proportional to ||S3||/||S1||, such as Y1, can be a more sensitive and robust detector of the impending worsening HF event than a HS metric such as S3 intensity alone, at least because of combined responses of S1 and S3 to the HF status. Likewise, when S1 intensity experiences a trend of growth (i.e., increase in intensity with time), a composite HS metric proportional to ||S3||*||S1||, such as Y2, can be a more sensitive and robust detector of the impending worsening HF event than S3 intensity alone. The selected composite metric Y can be used by the HF event detector circuit 230 to detect the HF status, such as a progression over time of HF. In an example, a worsening HF event is deemed detected if Y exceeds a specified HF detection threshold $Y_{TH}$.

In some examples, at least one of the first or second composite HS metric can be computed using a change, or a rate of change, of two HS metrics. For example, the first composite HS metric Y1 can be proportional to a ratio Δ||S3||/Δ||S1||, and the second composite HS metric Y2 can be proportional to a product Δ||S3||*Δ||S1||, where "Δ" denotes a change of the corresponding HS metric within a specified time interval.

In some examples, the HS component detector circuit 321 can alternatively or additionally detect other HS components, such as S1 or S4 heart sounds. The HS metric generator circuit 322 can be configured to determine HS metrics such as intensity measures or cardiac timing intervals using the detected S1 or S4 heart sounds. The blending circuit can compute the first composite HS metric (Y1) to be proportional to one of the intensity ratios ||S3||/||S2||, ||S4||/||S1||, or ||S4||/||S2||, among others. Likewise, the blending circuit can compute the second composite HS metric (Y2) to be proportional to one of the intensity products ||S3||*||S2||, ||S4||*||S1||, or ||S4||*||S2||, among others.

Figure 4:
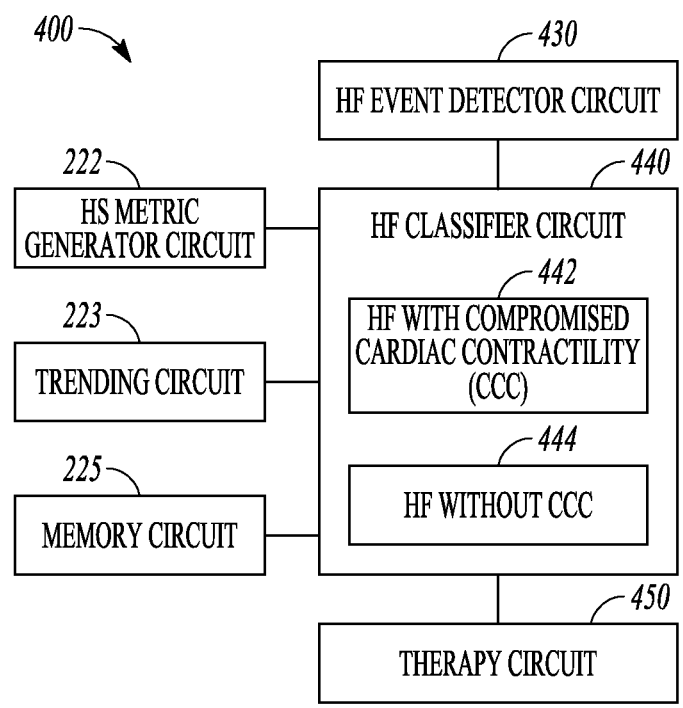
FIG. 4 illustrates generally an example of HF event classification system.

FIG. 4 illustrates generally an example of HF event classification system 400 for classifying a detected HF event. The HF event classification system 400 can be implemented as a part of, or as a system separate from, the HS-based physiologic event detector circuit 200.

The HF event classification system 400 can include a HF event detector circuit 430 to detect a HF event indicative of progression of heart failure (HF) status, such as a HF decompensation event or any event indicating worsening HF. In an example, HF event detector circuit 430 can be an embodiment of the HF event detector circuit 230. The HF event classification system 400 can include a HF event classifier circuit 440 that is communicatively coupled to one or both of the HS metric generator circuit 222 and the optional trending circuit 223, or alternatively coupled to the memory circuit 225 where the first and second HS metrics and the trend indicator are stored. As illustrated in FIG. 4, the HF event classifier circuit 440 can classify the detected HF event into one of a first category of HF with cardiac contractility compensation (CCC) 442, or a second category of HF without CCC 444, by using one or more HS metrics. The present inventors have recognized that, although some HF patients may have reduced cardiac contractility as the HF condition deteriorates, some other HF patients may have a compensated contractility as the HF condition progresses. For example, when the HF status worsens, more myocardium may be recruited through a mechanism of compensation for the heart to maintain sufficient cardiac output to the body. This can result in a compensatory increase in the cardiac contractility during the worsening of HF, and can be manifested as an increase in S1 intensity over time. Examples of HS metrics in patient with HF with cardiac contractility compensation (CCC) and with HF without CCC are discussed below, such as with reference to FIGS. 5A and 5B.

In an example, the HF classifier circuit 440 can use the S1 intensity ||S1|| such as produced by the HS metric generator circuit 222 or 322, or a ||S1|| trend indicator such as produced by the optional trending circuit 223 or 323, to classify the detected HF event. The detected HF event can be classified into the first category of HF with CCC if ||S1|| satisfies a first criterion, such as when ||S1|| indicates a growth trend. The detected HF event can be classified into the second category of HF without CCC if ||S1|| satisfies a second criterion, such as when ||S1|| indicates a decay trend. In another example, the HF event classification system 400 can use two or more HS metrics, such as both the S1 intensity ||S1|| and the S3 intensity ||S3|| such as produced by the HS metric generator circuit 222 or 322, or a joint S1-S3 trend indicator such as produced by the optional trending circuit 223 or 323, to classify the detected HF event. The detected HF event can be classified as HF with CCC if the joint S1-S3 trend satisfies a first criterion, such as when ||S1|| indicates a growth trend and ||S3|| indicates a concurrent growth trend, i.e., a joint S1-S3 trend ((||S3||$^+$, ||S1||$^+$). The detected HF event can be classified as HF without CCC if the joint S1-S3 trend satisfies a second criterion, such as when ||S1|| indicates a decay trend and ||S3|| indicates a concurrent growth trend, i.e., a joint S1-S3 trend ((||S3||$^+$, ||S1||$^-$).

In an example, the HF classifier circuit 440 can be coupled to the blending circuit 324, and classify the detected HF event using a composite HS metric, such as a composite HS metric proportional to a ratio of ||S3|| to ||S1||, or a composite HS metric proportional to a product of the intensity of ||S3|| and ||S1||. The HF classifier circuit 440 can classify the detected HF event into the first category of HF with CCC when the composite HS metric satisfies a first criterion, such as when composite metric $\|S3\|*\|S1\|$ exceeds a specified threshold. The HF classifier circuit 440 can classify the detected HF event into the second category of HF without CCC when the composite HS metric satisfies a second criterion, such as when the composite metric $\|S3\|/\|S1\|$ exceeds a specified threshold.

Compared to HF without CCC, HF with CCC may have different etiology, or indicates different phases of worsening of HF, and therefore may require different regimens of therapy. The therapy circuit 450, coupled to the HF classifier circuit 440, can be configured to deliver respective therapies to different classes of the HF events. Examples of the therapy can include electric pacing therapy, cardioversion therapy, defibrillation therapy, neuromodulation therapy, or other stimulation therapies using a specified energy source, or pharmacological therapies using medication or other specific therapeutic agents. In an example, compared to HF with CCC, more aggressive therapies can be recommended to the system user (e.g., a clinician), or automatically delivered to the patient in response to the detected HF event being classified as HF without CCC. The more aggressive therapy can include electrostimulation therapy with higher energy, higher intensity, or longer duration, or pharmacological therapy such as inotropic agents at different dosage. In some examples, the classification of the HF events can be presented to a system user, or a visual or audio alert signal can be produced in the output unit such as included in the user interface unit 250.

Figure 5A:
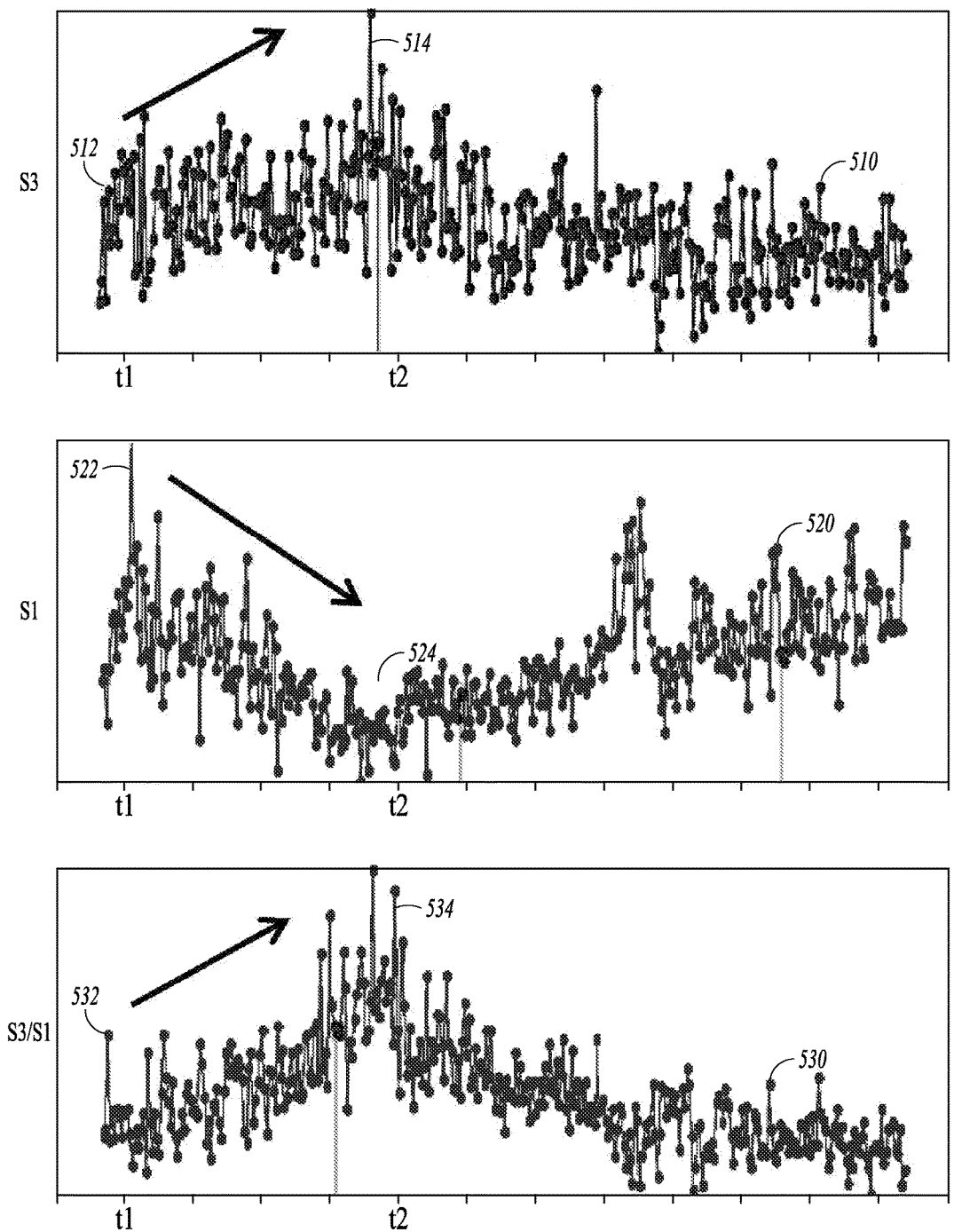
FIGS. 5A and 5B illustrate generally examples of HS metrics during a period of time leading to a worsening HF event.
Figure 5B:
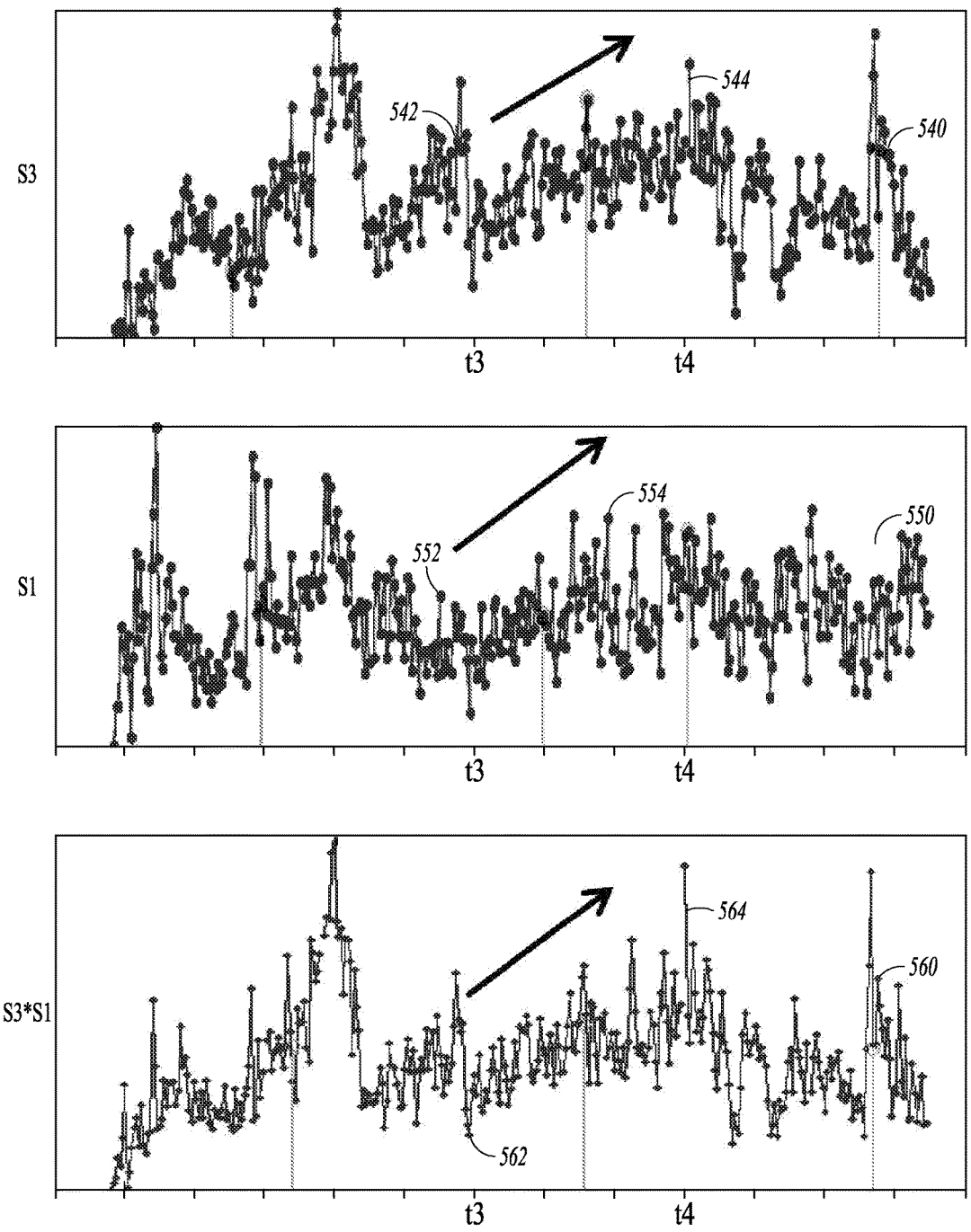

FIGS. 5A and 5B illustrate generally examples of trends of HS metrics during a period of time leading to a worsening HF event. The HS trends can be determined such as by using the HS processor circuit 220 or the HS processor circuit 320, and one or more of the trends as shown in FIGS. 5A and 5B can be displayed in a user interface unit 250 that allows a system user to review, annotate, or otherwise manipulate the trends.

FIG. 5A illustrates a first trend 510 of S3 intensity $\|S3\|$, a second trend 520 of S1 intensity $\|S1\|$, and a third trend 530 of a ratio of $\|S3\|$ to $\|S1\|$ (i.e., $\|S3\|/\|S1\|$), synchronously displayed over a specified period of time. Each data point in the trends 510, 520, or 530 represents value of the respective HS metric at the same cardiac cycle. For example, within a cardiac cycle at or about time instant t1 (on the x-axis which represents "time"), S1 and S3 heart sounds can be detected, and the respective intensity metric $\|S1\|_{t1}$ (522 on the $\|S1\|$ trend 520) and the intensity metric $\|S3\|_{t1}$ (512 on the $\|S3\|$ trend 520), as well as the composite metric $\|S3\|_{t1}/\|S1\|_{t1}$ (532 on the $\|S3\|/\|S1\|$ trend 530), can be determined, such as by using the HS processor circuit 220 or the HS processor circuit 320. In the example illustrated, within the time span from t1 to t2, there is a growth trend of $\|S3\|$ as manifested by an increase of $\|S3\|_{t1}$ at 512 to $\|S3\|_{t2}$ at 514, accompanied by a concurrent decay trend of $\|S1\|$ as manifested by a decreases of $\|S1\|_{t1}$ at 522 to $\|S1\|_{t2}$ at 524. As $\|S1\|$ can be correlated to, thus indicative of, the cardiac contractility, the increase of $\|S1\|$ from t1 to t2 suggests that cardiac contractility deteriorates without compensation. Because of the opposite trends of $\|S3\|$ and $\|S1\|$, the composite metric $\|S3\|/\|S1\|$ demonstrates a more prominent and steeper increase from $\|S3\|_{t1}/\|S1\|_{t1}$ to $\|S3\|_{t2}/\|S1\|_{t2}$. The composite metric selector 325, in response to the decay trend of $\|S1\|$, or the joint S1-S3 trend of concurrent decaying $\|S1\|$ and growing $\|S3\|$, can select the composite metric of ratio $\|S3\|/\|S1\|$, as opposed to the composite metric of product $\|S3\|*\|S1\|$, for detecting the impending worsening HF event. Compared to $\|S3\|$ alone, the composite metric $\|S3\|/\|S1\|$ has a higher rate of increase over time, making it a more sensitive and robust detector of worsening HF events in the scenario as illustrated in FIG. 5A. If a $\|S3\|/\|S1\|$ exceeds a detection threshold, an HF event is deemed detected. The HF classifier circuit 440 can classify the detected HF event as HF without CCC, such as based on the decay trend of $\|S1\|$.

Similar to FIG. 5A, FIG. 5B illustrates a S3 intensity trend 540, a S1 intensity trend 550, and a composite HS metric of $\|S3\|*\|S1\|$ trend 530 synchronously recorded and displayed over a specified period of time. Within the time span from t3 to t4, there is a growth trend of $\|S3\|$ from $\|S3\|_{t3}$ at 542 to $\|S3\|_{t4}$ at 544. However, in contrast to the $\|S1\|$ trend 520 of FIG. 5A, the concurrent $\|S1\|$ trend 550 is a growth trend that increases from $\|S1\|_{t3}$ at 552 to $\|S1\|_{t4}$ at 554. This may be a result of a compensated recovery of cardiac contractility. The composite metric selector 325, in response to the growth trend of $\|S1\|$, or the concurrent growth trends of $\|S1\|$ and $\|S3\|$, can select the composite metric of product $\|S3\|*\|S1\|$, as opposed to the composite metric of product $\|S3\|/\|S1\|$, for detecting the impending worsening HF event. Because of the same trends in $\|S3\|$ and $\|S1\|$, the composite metric $\|S3\|*\|S1\|$ can have a more prominent and steeper increase during the time period from t3 to t4, which makes the metric $\|S3\|*\|S1\|$ a more sensitive and robust detector of worsening HF events in the scenario as illustrated in FIG. 5B. If $\|S3\|*\|S1\|$ exceeds a detection threshold, a HF event is deemed detected. The HF classifier circuit 440 can then classify the HF event as HF with CCC, such as based on the growth trend of $\|S1\|$.

Figure 6:
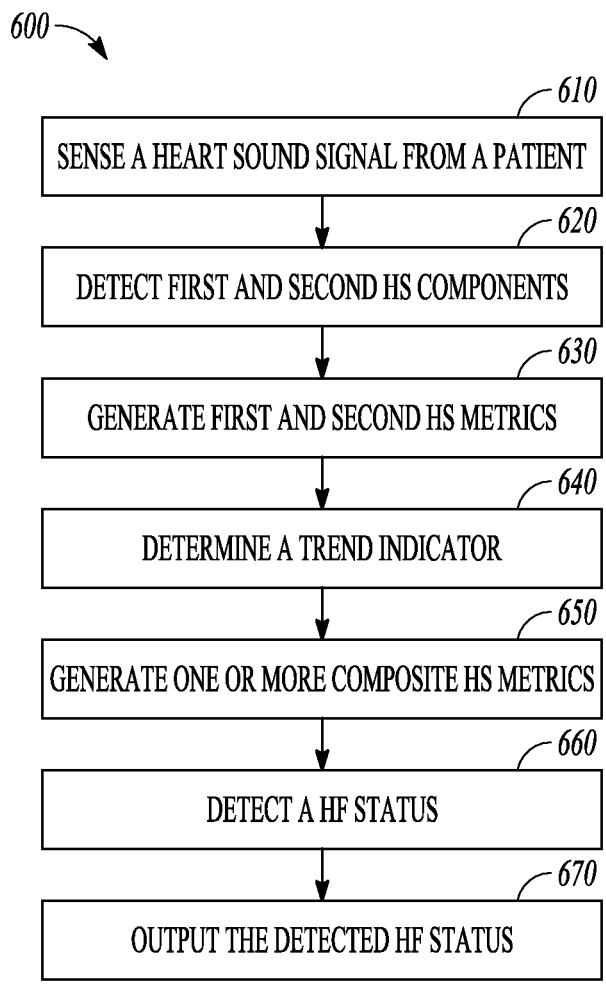
FIG. 6 illustrates generally an example of a method for detecting a target event indicative of progression of HF status in a patient using a HS signal.

FIG. 6 illustrates generally an example of a method 600 for detecting a target event indicative of progression of HF status in a patient using a heart sound (HS) signal. The target event can include HF decompensation event or other worsening HF events. The method 600 can be implemented and operate in an ambulatory medical device such as an implantable or wearable medical device, or in a remote patient management system. In an example, the method 600 can be performed by the HS-based HF event detector 113 such as implemented in the IMD 110, or the external system 120 in communication with the IMD 110.

The method 600 begins at 610 by sensing a HS signal from a patient. The HS signal can be sensed using an implantable, wearable, or otherwise ambulatory sensor that can be configured to sense acoustic or mechanical activity of a heart. The sensed HS signal can be pre-processed, including amplification, digitization, filtering, or other signal conditioning operations, such as to improve the signal to noise ratio to facilitate detection of HS components.

At 620, at least a first and a different second HS components can be detected from the sensed HS signal. The HS components can include S1, S2, S3, or S4 heart sounds. In an example, the HS components can be detected within respectively defined HS detection window, such as S1 window, S2 window, S3 window, or S4 window. A HS component is detected if the HS signal energy calculated with the respective HS detection window exceeds a specified threshold. In another example, the HS component can be adaptively detected by tracking the temporal locations of the previously detected HS component.

At 630, at least a first and second HS metrics can be generated using the respective first and second HS components. The HS metrics can include temporal, statistical, or morphological features of one or more HS components. In an example, the HS metrics can include S1 intensity ($\|S1\|$), S2 intensity ($\|S2\|$), S3 intensity ($\|S3\|$), or S4 intensity ($\|S4\|$). The intensity can be measured as amplitude in the time domain for peak spectral density in a frequency domain. In another example, the HS metrics can include cardiac timings such as cardiac timing interval (CTI) measured between a cardiac electrical event such as detected from the cardiac electrical signal and a mechanical event such as detected from the HS signal. The CTI can include a pre-ejection period (PEP), a systolic timing interval (STI), or a diastolic timing interval (DTI), among others.

The method 600 can include an optional step at 640, where a HS trend indicator can be generated using a plurality of measurements of the first or second HS metrics, such as over multiple cardiac cycles or during a specified period of time. In an example, the trend indicator can be obtained from one HS metric, such as S1 intensity or S3 trend. The trend indicator can include a growth trend indicating an increase of a HS metric over time, or a decay trend indicating a decrease of the HS metric over time. In another example, the trend indicator can be obtained from two or more HS metrics, such as both S1 intensity and S3 intensity. The trend indicator thus generated can indicate a covariation temporal pattern between the two or more HS metrics.

At 650, one or more composite HS metric can be generated. Each composite HS metric can be produced using two or more HS metrics. The composite HS metric can be a linear or nonlinear function of the two or more HS metrics. In an example, the generation of composite HS metrics can be based on the HS trend indicator as produced at 640. In an example, a first composite HS metric can be generated when the trend indicator indicates a first trend, or a different second composite HS metric can be generated when the trend indicator indicates a different second trend.

At 660, a target HF status, such as worsening HF, can be detected. In an example, the detection of the HF status can include trending the selected composite HS metric over time. The trend of the selected composite HS metric can be compared to a specified criterion, such as a threshold or a value range, to detect the target HF status. When the target HF status is deemed detected, at 670 the information including the detection of the target HF status can be presented at an output device such as the user interface unit 250. In an example, the output information can be presented in a table, a chart, a diagram, or any other types of textual, tabular, or graphical presentation formats. In an example, an alert can be produced if a worsening HF is detected. The alert can be in audio or other human-perceptible media format. Additionally or alternatively, the method 600 can include delivering a therapy, such as electrostimulation therapy delivered to the heart or neural targets, in response to the HF status satisfying a specified condition.

Figure 7:
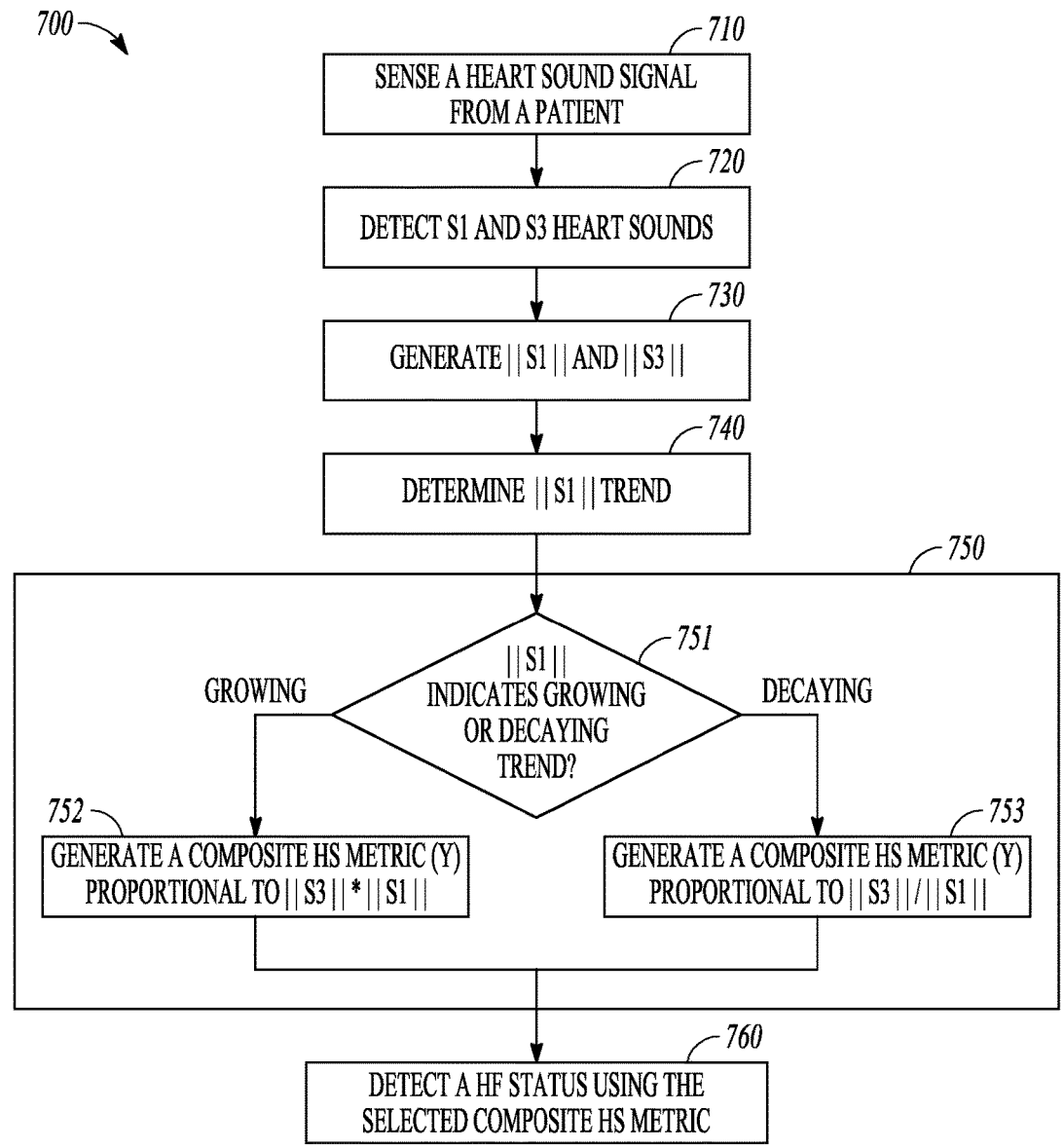
FIG. 7 illustrates generally an example of a method for detecting a target event indicative of progression of HF status using S1 and S3 heart sounds.

FIG. 7 illustrates generally an example of a method 700 for detecting a target event indicative of progression of HF status using S1 and S3 heart sounds. The method 700 can be an embodiment of the method 600. In an example, the method 700 can be implemented in and executed by the physiologic target event detector 200 as illustrated in FIG. 2.

The method 700 begins at 710 by sensing a HS signal from a patient. From the HS signal, S1 and S3 heart sound components can be detected at 720, such as using respective S1 detection window and S3 detection window. In an example, the S1 detection window can begin at 50 milliseconds (msec) following a detected R wave of a ECG signal and have a duration of 300 msec. An S2 detection window can begin at specified offset following a detected R wave or S1 heart sound. An S3 detection window can be determined using at least one cardiac signal feature such as the R-wave timing or the timing of S2 heart sound. The S3 detection window can have a specified duration and can begin at a specified offset following the detected S2. In an example, the offset can be 125 msec, and the S3 window duration can be 125 msec. Alternatively, the S3 heart sound can be detected by adaptively tracking the timing of historically detected S3 heart sounds. Intensities of the detected S1 and S3 heart sounds, such as the peak amplitude, can be determined at 730.

At 740, a $\|S1\|$ trend can be generated, such as by using the optional trending circuit 223 or the optional trending circuit 323. The $\|S1\|$ trend can be generated using a plurality of S1 intensity measurements $\{\|S1\|_i\}$ for i=1, 2, . . . M, such as over M cardiac cycles or during a specified period of time no shorter than M cardiac cycles. A growing $\|S1\|$ trend can be demonstrated by increase in $\|S1\|$ over time or a positive slope of change of $\|S1\|$, and a decaying $\|S1\|$ trend can be demonstrated by decrease in $\|S1\|$ over time or a negative slope of change of $\|S1\|$.

At 750, either a first or a different second composite HS metric can be generated, such as by using the composite HS metric generator 224 or the composite HS metric generator 324. The step 750, as an embodiment of the step 650 of method 600, can include a step 751 for selecting between the first and second composite HS metrics based on the trend of $\|S1\|$ produced at 740. If the $\|S1\|$ indicates a growth trend, then at 752, a composite HS metric Y that is proportional to a product of $\|S3\|$ and $\|S1\|$ can be generated, that is, Y=b*$\|S3\|$*$\|S1\|$. Alternatively, instead of using the composite HS metric b*$\|S3\|$*$\|S1\|$, the HS metric $\|S3\|$ can be used, that is, Y=b*$\|S3\|$. However, if the $\|S1\|$ indicates a decay trend, then at 753, a composite HS metric that is proportional to a ratio of $\|S3\|$ to $\|S1\|$ can be generated, that is, Y=a*$\|S3\|$/$\|S1\|$. Then at 760, the selected composite metric Y can then be used to detect the HF status. In an example, a worsening HF event is deemed detected if Y exceeds a specified HF detection threshold $Y_{TH}$. In some examples, the selected composite metric Y can be combined with one or more other HS metrics or other physiological signal metrics to detect the HF status at 760. In an example, the HF status can be detected using an average of a*$\|S3\|$/$\|S1\|$ and $\|S3\|$, that is, (a*$\|S3\|$/$\|S1\|$+$\|S3\|$)/2.

Figure 8:
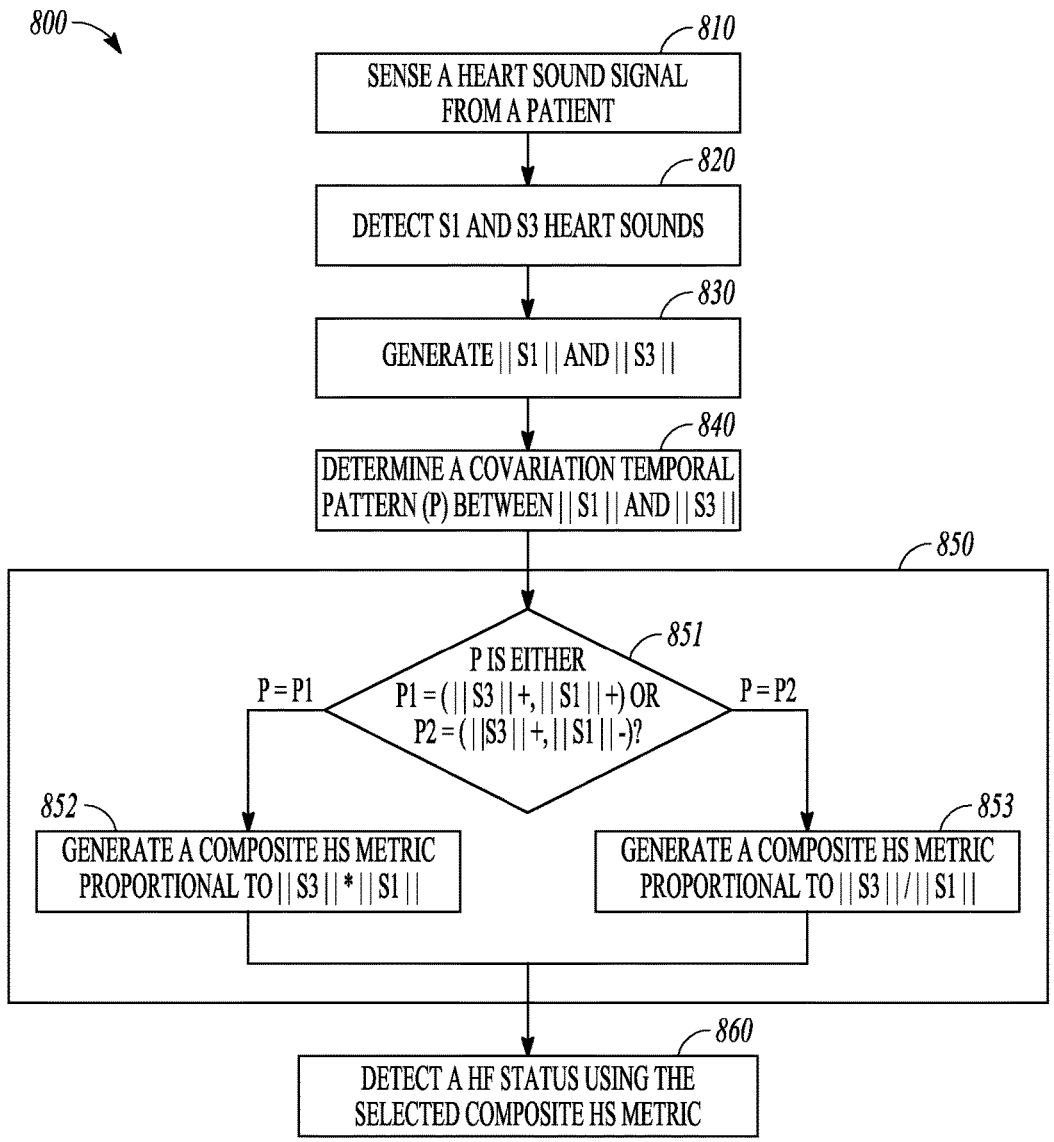
FIG. 8 illustrates generally another example of a method for detecting a target event indicative of progression of HF status using S1 and S3 heart sounds.

FIG. 8 illustrates generally another example of a method 800 for detecting a target event indicative of progression of HF status using S1 and S3 heart sounds. The method 800 can be an embodiment of the method 600. In an example, the method 800 can be implemented in and executed by the physiologic target event detector 200 as illustrated in FIG. 2.

Similar to steps 710-730 of the method 700, the method 800 can comprise steps 810-830 for sensing a HS signal from a patient, detecting S1 and S3 heart sound components from the sensed HS signal, and generating the intensities of the detected S1 and S3 heart sounds, such as the peak amplitudes. At 840, a covariation temporal pattern between $\|S1\|$ and $\|S3\|$ can be determined. The covariation temporal pattern can be represented as a combination of the temporal patterns of the two or more HS metrics during the same specified period of time. In an example, the covariation temporal pattern can include a joint S1-S3 trend indicator, such as a decay trend of $\|S1\|$ (denoted by $\|S1\|^-$) concurrent with a growth trend of $\|S3\|$ (denoted by $\|S3\|^+$). Similar to the determination of $\|S1\|$ trend at 740, a growing $\|S3\|$ trend can be demonstrated by increase in $\|S3\|$ over time or a positive slope of change of $\|S3\|$, and a decaying $\|S3\|$ trend can be demonstrated by decrease in $\|S3\|$ over time or a negative slope of change of $\|S3\|$. In another example, the covariation temporal pattern can be represented as correlation between the two or more HS metrics, where a positive correlation indicates same trend among the two or more HS metrics, and a negative correlation indicates opposite trends among the two or more HS metrics.

At 850, either a first or a different second composite HS metric can be generated, such as by using the composite HS metric generator 224 or the composite HS metric generator 324. As illustrated in FIG. 8, the step 850 can include a decision process at 851 for selecting between the first and second composite HS metrics based on the covariation temporal pattern (P). In an example, if the covariation temporal pattern indicates a first joint S1-S3 trend indicator of a growth trend of $\|S1\|$ concurrent with a growth trend of $\|S3\|$, then at 852 a first composite HS metric proportional to a product of $\|S3\|$ and $\|S1\|$ can be selected. Alternatively, instead of using the composite HS metric, the HS metric $\|S3\|$ can be selected. However, if the covariation temporal pattern indicates a different second joint S1-S3 trend indicator of a decay trend of $\|S1\|$ concurrent with a growth trend of $\|S3\|$, then at 853 a second composite HS metric proportional to a ratio of $\|S3\|$ to $\|S1\|$ can be selected. Then at 860, the selected composite metric (Y) can then be used to detect the HF status. In an example, a worsening HF event is deemed detected if Y exceeds a specified HF detection threshold $Y_{TH}$. The selected composite metric Y can be combined with one or more other HS metrics or other physiological signal metrics to detect the HF status at 760, such as an average of $a*\|S3\|/\|S1\|$ and $\|S3\|$, that is, $(a*\|S3\|/\|S1\|+\|S3\|)/2$.

Figure 9:
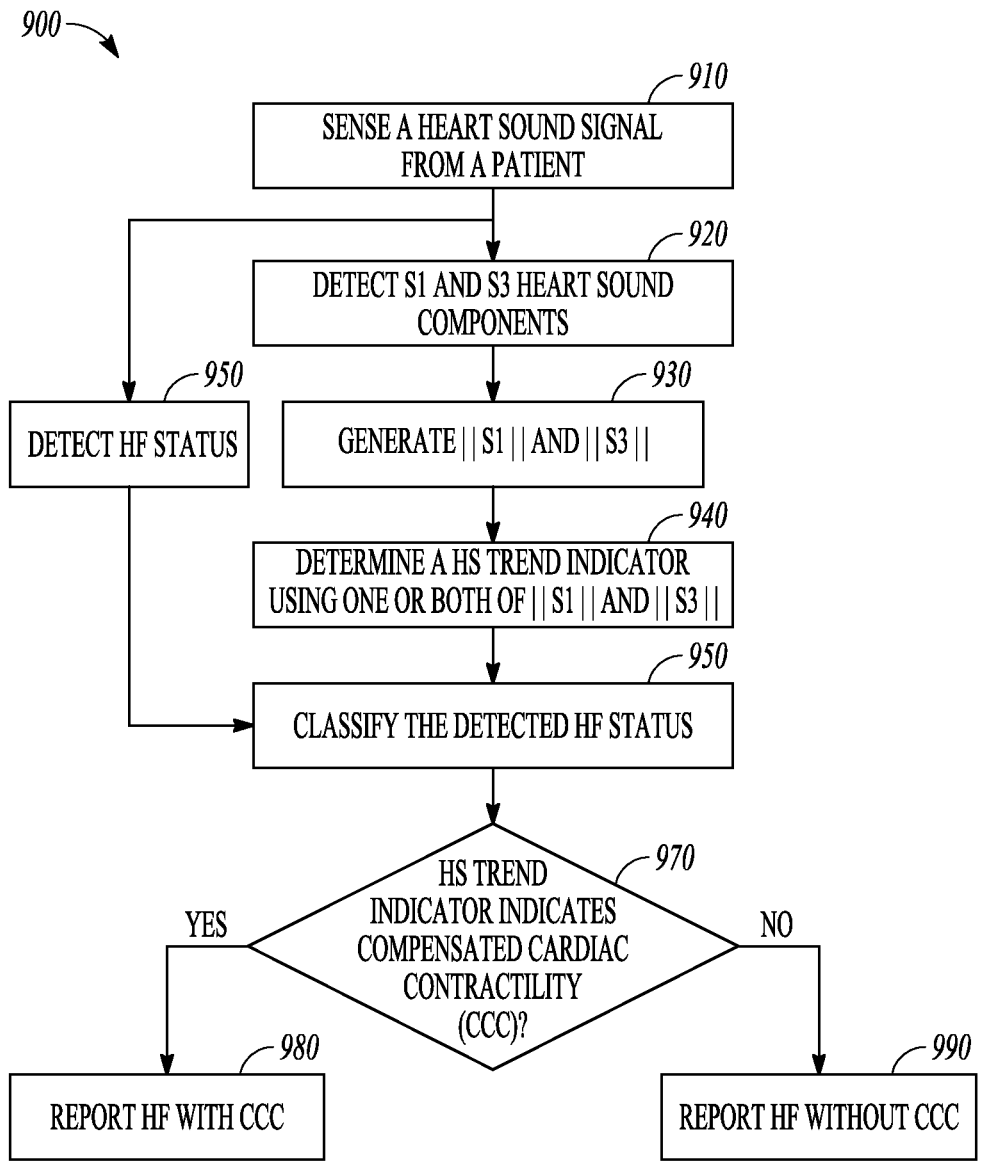
FIG. 9 illustrates generally an example of a method for classifying a HF event using a HS signal.

FIG. 9 illustrates generally an example of a method 900 for classifying a HF event using a HS signal. The method 900 can be used by the HF event classification system 400. The method 900 can be implemented in and operated by an ambulatory medical device such as an implantable or wearable medical device, or in a remote patient management system. In an example, the method 900 can be performed by the HS-based HF event detector 113 such as implemented in the IMD 110, or the external system 120 in communication with the IMD 110.

Similar to the steps 710-730 of the method 700 or the steps 810-830 of the method 800, the method 900 can include steps 910-930 for sensing a HS signal from a patient, detecting S1 and S3 heart sound components from the sensed HS signal, and generating the intensities of the detected S1 and S3 heart sounds, such as the peak amplitudes. At 940, a HS trend indicator can be generated using one or both of $\|S1\|$ and $\|S3\|$. In an example, the HS trend indicator can include a $\|S1\|$ trend such as produced at step 740 of the method 700. In another example, the HS trend indicator can include a covariation temporal pattern between $\|S1\|$ and $\|S3\|$, such as a joint S1-S3 trend indicator as produced at step 840 of the method 800.

At 950, a HF event, such as a HF decompensation event or any event indicating worsening HF, can be detected. The detection of the HF event can be based on one of the methods 600, 700, or 800 disclosed in this document. Alternatively, the HF event can be detected using other methods based on at least one physiological signal other than heart sounds signal, such as based on thoracic impedance signal, respiration signal, physical activity signal, or any other physiological signals. Alternatively, instead of detecting the HF event, the step 950 can include receiving information, such as an indication from a user, that the HF event (such as worsening HF) is detected, and the heart sound signal is sensed at 910 from the patient having an indication of the target HF event.

At 960, the detected HF event from 950 can be classified into one of two or more classes of HF status using one or more HS metrics such as provided at 940. In an example, the classes can include a first category of HF with cardiac contractility compensation (CCC), or a second category of HF without CCC. At 970, the HS trend indicator can be compared to a specified criterion to determine which class the detected HF status should belong to. In an example, the detected HF event can be classified into the first category of HF with CCC if $\|S1\|$ satisfies a first criterion, such as when $\|S1\|$ indicates a growth trend, or when the rate of change of $\|S1\|$, such as measured as a slope of $\|S1\|$ over time, exceeds a specified threshold. The detected HF event can be classified into the second category of HF without CCC when $\|S1\|$ satisfies a second criterion, such as when $\|S1\|$ indicates a decay trend, or when the rate of change of $\|S1\|$ fails to exceed a specified threshold. In another example, the detected HF event can be classified into the first category of HF with CCC if a joint S1-S3 trend indicator satisfies a first criterion, such as when $\|S1\|$ indicates a growth trend and $\|S3\|$ indicates a concurrent growth trend, or when a correlation between $\|S1\|$ trend and the $\|S3\|$ trend exceeds a specified threshold. The detected HF event can be classified as HF without CCC when the joint S1-S3 trend satisfies a second criterion, such as when $\|S1\|$ indicates a decay trend and $\|S3\|$ indicates a concurrent growth trend, or when the correlation between $\|S1\|$ trend and the $\|S3\|$ trend fails to exceed the specified threshold.

If the detected HF event is classified as a HF with CCC, then at 980, a report including the classification result can be generated and presented to a system user, such as via a displaying unit or a user interface unit. Likewise, if the detected HF event is classified as a HF without CCC, then at 990, a corresponding report including that classification result can be generated and presented to the system user. Other visual or audio signal can alternatively or additionally be produced to alert the system user about the classification. In some examples, the method 900 can include delivering respective therapies upon a classification of the HF events. In an example, more aggressive therapies can be delivered to the patient if the HF event is classified as HF without CCC. The more aggressive therapy can include electrostimulation therapy with higher energy, higher intensity, or longer duration, or pharmacological therapy with different pharmaceutical agents and/or different dosage.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system, comprising:
a signal sensor circuit, including a sense amplifier circuit to sense a heart sound (HS) signal from a patient;
a memory circuit;
a HS component detector circuit, coupled to the signal sensor circuit and the memory circuit to detect at least first and different second HS components from the received HS signal;
a HS metric generator circuit, coupled to the HS component detector circuit to use the detected first and second HS components to respectively generate first and second HS metrics stored in the memory circuit;
a blending circuit, coupled to the memory circuit or the HS metric generator circuit to generate one or more composite HS metrics using a ratio of the second HS metric to the first HS metric or a product of the first and second HS metrics;
a heart failure (HF) event detector circuit, including a comparator circuit coupled to the blending circuit to detect a worsening HF status using a combination of (1) at least one of the first or second HS metric and (2) at least one of the one or more composite HS metrics; and
an output circuit configured to output an indication of the worsening HF status.

2. The system of claim 1, further comprising a trending circuit coupled to the HS metric generator circuit, the trending circuit configured to determine a trend indicator stored in the memory circuit, the trend indicator indicating a temporal pattern of at least one of the first or second HS metric,
wherein the blending circuit is configured to selectively generate the one or more composite HS metrics according to the trend indicator.

3. The system of claim 2, wherein the blending circuit is configured to selectively generate the one or more composite HS metrics including a first composite HS metric when the trend indicator indicates a first trend, or a different second composite HS metric when the trend indicator indicates a different second trend.

4. The system of claim 3, wherein:
the HS component detector circuit is configured to detect the first HS component including a S1 or S2 heart sound, and the second HS component including a S3 or S4 heart sound; and
the HS metric generator circuit is configured to generate the first HS metric indicative of intensity of the detected S1 or S2 heart sound, and the second HS metric indicative of intensity of the detected S3 or S4 heart sound.

5. The system of claim 4, wherein the HS metric generator circuit is configured to generate the first HS metric including an amplitude of S1 heart sound, and the second HS metric including an amplitude of S3 or S4 heart sound.

6. The system of claim 4, wherein:
the trending circuit is configured to determine the trend indicator including a S1 intensity trend indicating a decay trend or a growth trend of the S1 intensity over a specified period of time; and
the blending circuit is configure to selectively generate:
the first composite HS metric that is proportional to a ratio of the intensity of S3 or S4 heart sound to the intensity of S1 heart sound if the trend indicator indicates a decay trend of the intensity of S1 heart sound; or the second composite HS metric that is proportional to a product of the intensity of S3 or S4 heart sound and the intensity of S1 heart sound if the trend indicator indicates a growth trend of the intensity of S1 heart sound.

7. The system of claim 4, wherein:
the trending circuit is configured to determine the trend indicator including a covariation temporal pattern between the intensity of S1 heart sound and the intensity of the S3 or S4 heart sound over a specified period of time; and
the blending circuit is configure to selectively generate:
the first composite HS metric that is proportional to a ratio of the intensity of S3 or S4 heart sound to the intensity of S1 heart sound if the trend indicator indicates a growth trend of S3 or S4 intensity concurrent with a decay trend of S1 intensity; or the second composite HS metric that is proportional to a product of the intensity of S3 or S4 heart sound and the intensity of S1 heart sound if the trend indicator indicates a growth trend of S3 or S4 intensity concurrent with a growth trend of S1 intensity.

8. The system of claim 1, further comprising a classifier circuit configured to classify the detected worsening HF status into one of a first category of HF with cardiac contractility compensation (CCC), or a second category of HF without CCC.

9. The system of claim 8, wherein:
the HS metric generator circuit is configured to generate the first HS metric including a S1 intensity; and
the classifier circuit is configured to classify the detected worsening HF status into the first category of HF with CCC if the S1 intensity satisfies a first criterion, or to classify the detected worsening HF status into the second category of HF without CCC if the S1 intensity satisfies a second criterion.

10. The system of claim 8, wherein:
the HS metric generator circuit is configured to generate the composite HS metric proportional to a ratio of the intensity of S3 or S4 heart sound to the intensity of S1 heart sound, or proportional to a product of the intensity of S3 or S4 heart sound and the intensity of S1 heart sound; and
the classifier circuit is configured to classify the detected worsening HF status into the first category of HF with CCC if the composite HS metric satisfies a first criterion, or to classify the detected worsening HF status into the second category of HF without CCC if the composite HS metric satisfies a second criterion.

11. The system of claim 1, wherein the signal sensor circuit is further configured to receive a physiological signal sensed from the patient, the physiological signal different from the HS signal and indicative of cardiac contractility.

12. The system of claim 1, further comprising a therapy circuit configured to deliver a therapy to the patient in response to the worsening HF status satisfying at least one condition.

13. The system of claim 12, wherein the therapy circuit is configured to deliver a first therapy in response to a detection of HF with cardiac contractility compensation (CCC), or deliver a second therapy in response to a detection of HF without CCC, the second therapy being more aggressive than the first therapy.

14. A method, comprising:
sensing a heart sound (HS) signal from a patient using a HS sensor;
detecting at least a first and a different second HS components from the sensed HS signal;
generating first and second HS metrics respectively from the detected first and second HS components;
generating one or more composite HS metrics using a ratio of the second HS metric to the first HS metric or a product of the first and second HS metrics;
detecting a worsening HF status using a combination of (1) at least one of the first or second HS metric and (2) at least one of the one or more composite HS metrics; and
outputting an indication of the detected worsening HF status.

15. The method of claim 14, further comprising determining a trend indicator indicating a temporal pattern of at least one of the first or second HS metric,
wherein generating the one or more composite HS metrics includes:
generating a first composite HS metric when the trend indicator indicates a first trend; or
generating a different second composite HS metric when the trend indicator indicates a different second trend.

16. The method of claim 15, wherein:
detecting the first HS component includes detecting a S1 heart sound, and detecting the second HS component including detecting a S3 or S4 heart sound; and
generating the first HS metric includes generating an intensity metric of the detected S1 heart sound, and generating the second HS metric includes generating an intensity metric of the detected S3 or S4 heart sound.

17. The method of claim 16, wherein:
determining the trend indicator includes determining a S1 intensity trend indicating a temporal pattern of the intensity of S1 heart sound over a specified period of time; and
generating the one or more composite HS metrics includes:
generating the first composite HS metric that is proportional to a ratio of the intensity of S3 or S4 heart sound to the intensity of S1 heart sound, when the trend indicator indicates a decay trend of the intensity of S1 heart sound; or
generating the second composite HS metric that is proportional to a product of the intensity of S3 or S4 heart sound and the intensity of S1 heart sound, when the trend indicator indicates a growth trend of the intensity of S1 heart sound.

18. The method of claim 16, wherein:
determining the trend indicator includes determining a covariation temporal pattern between the intensity of S1 heart sound and the intensity of the S3 or S4 heart sound over a specified period of time; and
generating the one or more composite HS metrics includes:
generating the first composite HS metric that is proportional to a ratio of the intensity of S3 or S4 heart sound to the intensity of S1 heart sound, when the trend indicator indicates a growth trend of S3 or S4 intensity concurrent with a decay trend of S1 intensity; or
generating the second composite HS metric that is proportional to a product of the intensity of S3 or S4 heart sound and the intensity of S1 heart sound, when the trend indicator indicates a growth trend of S3 or S4 intensity concurrent with a growth trend of S1 intensity.

19. The method of claim 14, further comprising:
classifying the detected worsening HF status into a first category of HF with cardiac contractility compensation (CCC) if a HS metric satisfies a first criterion; or
classifying the detected worsening HF status into a second category of HF without CCC if the HS metric satisfies a second criterion.

20. The method of claim 19, wherein classifying the detected worsening HF status includes:
classifying the detected worsening HF status into the first category of HF with CCC if the S1 intensity has a growth trend over time; or
classifying the detected worsening HF status into the second category of HF without CCC if the S1 intensity has a decay trend over time.

* * * * *